US008017590B1

(12) United States Patent
Berinstein et al.

(10) Patent No.: US 8,017,590 B1
(45) Date of Patent: Sep. 13, 2011

(54) METHOD OF INDUCING AND/OR ENHANCING AN IMMUNE RESPONSE TO TUMOR ANTIGENS

(75) Inventors: Neil Berinstein, Toronto (CA); James Tartaglia, Schenectady, NY (US); Philippe Moingeon, Pommiers (FR); Brian Barber, Mississauga (CA)

(73) Assignee: Sanofi Pasteur Limited, Toronto, Ontario (CA)

( * ) Notice: Subject to any disclaimer, the term of this patent is extended or adjusted under 35 U.S.C. 154(b) by 0 days.

(21) Appl. No.: 09/693,754

(22) Filed: Oct. 20, 2000

Related U.S. Application Data

(60) Provisional application No. 60/160,879, filed on Oct. 22, 1999, provisional application No. 60/223,325, filed on Aug. 7, 2000.

(51) Int. Cl.
*A61K 48/00* (2006.01)
*A61K 38/00* (2006.01)
*A61K 38/04* (2006.01)
*A61K 39/00* (2006.01)

(52) U.S. Cl. ............... 514/44 R; 424/184.1; 424/185.1; 424/199.1; 424/93.21

(58) Field of Classification Search ............ 514/2, 44 R, 514/44; 424/93.2, 184.1, 185.1, 199.1, 93.21; 435/325, 320.1; 530/300, 350
See application file for complete search history.

(56) References Cited

U.S. PATENT DOCUMENTS

| 4,603,112 A | 7/1986 | Paoletti et al. ............... 435/235 |
| 4,722,848 A | 2/1988 | Paoletti et al. ................ 424/89 |
| 4,769,330 A | 9/1988 | Paoletti et al. ............. 435/172.3 |
| 4,882,278 A | 11/1989 | Mekalanos ............... 435/172.3 |
| 5,093,258 A | 3/1992 | Cohen et al. |
| 5,110,587 A | 5/1992 | Paoletti et al. ................. 424/89 |
| 5,141,742 A | 8/1992 | Brown et al. |
| 5,174,993 A | 12/1992 | Paoletti ........................ 424/89 |
| 5,185,146 A | 2/1993 | Altenburger .................. 424/89 |
| 5,342,774 A | 8/1994 | Boon et al. ................. 435/240.2 |
| 5,348,887 A | 9/1994 | Bumol et al. ............. 435/320.1 |
| 5,364,773 A | 11/1994 | Paoletti et al. .............. 435/69.1 |
| 5,378,457 A | 1/1995 | Paoletti et al. ............. 424/205.1 |
| 5,405,940 A | 4/1995 | Boon et al. |
| 5,462,871 A | 10/1995 | Boon-Falleur et al. |
| 5,494,807 A | 2/1996 | Paoletti et al. .............. 435/69.3 |
| 5,505,941 A | 4/1996 | Paoletti ..................... 424/93.2 |
| 5,698,530 A | 12/1997 | Schlom et al. ................. 514/44 |
| 5,739,026 A | 4/1998 | Garoff et al. ............. 435/240.2 |
| 5,756,103 A | 5/1998 | Paoletti et al. ............ 424/199.1 |
| 5,762,938 A | 6/1998 | Paoletti et al. ............ 424/199.1 |
| 5,789,245 A | 8/1998 | Dubensky, Jr. et al. .... 435/320.1 |
| 5,792,462 A | 8/1998 | Johnston et al. .......... 424/199.1 |
| 5,804,381 A | 9/1998 | Chen et al. ..................... 435/6 |
| 5,831,016 A | 11/1998 | Wang et al. ................. 530/350 |
| 5,833,975 A | 11/1998 | Paoletti et al. ............ 424/93.2 |
| 5,840,839 A | 11/1998 | Wang et al. |
| 5,843,723 A | 12/1998 | Dubensky, Jr. et al. ...... 435/69.3 |
| 5,844,075 A | 12/1998 | Kawakami et al. |
| 5,869,445 A | 2/1999 | Cheever et al. .................... 514/2 |
| 5,874,560 A | 2/1999 | Kawakami et al. .......... 536/23.5 |
| 5,932,210 A | 8/1999 | Gregory et al. .............. 424/93.2 |
| 5,972,597 A | 10/1999 | Paoletti et al. |
| 5,990,091 A | 11/1999 | Tartaglia et al. ................ 514/44 |
| 5,994,132 A | 11/1999 | Chamberlain et al. ........ 435/369 |
| 6,001,349 A | 12/1999 | Panicali et al. |
| 6,045,802 A | 4/2000 | Schlom et al. |
| 6,057,158 A | 5/2000 | Chamberlain et al. ........ 435/456 |
| 6,083,703 A | 7/2000 | Wang et al. ....................... 435/6 |
| 6,087,110 A | 7/2000 | Wang et al. |
| 6,127,116 A * | 10/2000 | Rice et al. .......................... 435/6 |
| 6,132,980 A | 10/2000 | Wang et al. |
| 6,235,525 B1 | 5/2001 | Vanden Eynde et al. ..... 435/325 |
| 6,319,496 B1 | 11/2001 | Panicali et al. |
| 6,340,462 B1 | 1/2002 | Paoletti |
| 6,407,063 B1 | 6/2002 | Luiten et al. |
| 6,531,451 B1 | 3/2003 | Chaux et al. |
| 6,548,068 B1 | 4/2003 | Schlom et al. |
| 6,558,671 B1 | 5/2003 | Slingluff et al. |
| 6,693,086 B1 | 2/2004 | Dow et al. |
| 6,699,475 B1 | 3/2004 | Panicali et al. |
| 6,709,844 B1 | 3/2004 | Levy |
| 6,710,172 B1 | 3/2004 | Chaux et al. |
| 6,756,038 B1 | 6/2004 | Schlom et al. |
| 6,780,407 B1 | 8/2004 | Paoletti et al. |
| 6,805,869 B2 | 10/2004 | Guo |
| 6,861,234 B1 | 3/2005 | Simard et al. |
| 6,893,869 B2 | 5/2005 | Schlom et al. |
| 6,951,917 B1 | 10/2005 | Topalian et al. |
| 6,969,609 B1 | 11/2005 | Schlom et al. |

(Continued)

FOREIGN PATENT DOCUMENTS

EP 584266 3/1994

(Continued)

OTHER PUBLICATIONS

Salgaller et.al.; Immunuization against Epitopes in the Human Melanoma Antigen gp100 following Patent Immunization with Synthetic Peptides, 1996, Cancer Research 56: 4749-4757.*
Zaremba et.al.; Identification of an Enhancer Agonist Cytotoxic T Lymphocyte Peptide from Human Carcinoembryonic Antigen, 1997, Cancer Research 57: 4570-4577.*
Hurpin et.al.; The mode of presentation and route of administration are critical for the induction of immune responses to p53 and antitumor immunity, 1998, Vaccine, vol. 16, No. 2/3: 208-215.*
Hodge et al. (1997) Vaccine, vol. 15, No. 6/7, 759-768.*

(Continued)

*Primary Examiner* — Anne Marie S Wehbe
(74) *Attorney, Agent, or Firm* — Patrick J. Halloran; Reza Yacoob

(57) ABSTRACT

An improved method of inducing and/or enhancing an immune response to a tumor antigen is disclosed. The method involves administering the tumor antigen, nucleic acid coding therefor, vectors and/or cells comprising said nucleic acid, or vaccines comprising the aforementioned to a lymphatic site.

31 Claims, 11 Drawing Sheets

U.S. PATENT DOCUMENTS

| | | | |
|---|---|---|---|
| 6,977,074 | B2 | 12/2005 | Kundig et al. |
| 6,994,851 | B1 | 2/2006 | Kundig et al. |
| 7,231,887 | B2 | 6/2007 | Havermans et al. |
| 7,232,682 | B2 | 6/2007 | Simard et al. |
| 7,364,729 | B2 | 4/2008 | Kundig et al. |
| 7,390,654 | B2 | 6/2008 | Levy |
| 2002/0025578 | A1 | 2/2002 | MacLaughlin et al. |
| 2003/0022854 | A1* | 1/2003 | Dow et al. ............... 514/44 |
| 2003/0082150 | A1 | 5/2003 | Boon-Falleur et al. |
| 2004/0156861 | A1 | 8/2004 | Figdor et al. |
| 2005/0136066 | A1 | 6/2005 | Guo |

FOREIGN PATENT DOCUMENTS

| | | |
|---|---|---|
| EP | 1083232A1 A1 | 3/2001 |
| WO | WO 88/06626 | 9/1988 |
| WO | WO 90/00594 | 1/1990 |
| WO | WO 91/13157 | 9/1991 |
| WO | WO 92/01796 | 2/1992 |
| WO | WO 92/10578 | 6/1992 |
| WO | WO 92/11354 | 7/1992 |
| WO | WO 92/11361 | 7/1992 |
| WO | WO 92/19266 | 11/1992 |
| WO | WO 92/21376 | 12/1992 |
| WO | WO 94/01533 | 1/1994 |
| WO | WO 94/19482 | 9/1994 |
| WO | WO 95/04542 | 2/1995 |
| WO | WO 95/23234 | 8/1995 |
| WO | WO 95/25530 | 9/1995 |
| WO | WO 95/25739 | 9/1995 |
| WO | WO 95/27044 | 10/1995 |
| WO | WO 96/11279 | 10/1995 |
| WO | WO 95/29193 | 11/1995 |
| WO | WO 95/31565 | 11/1995 |
| WO | WO 96/21734 | 7/1996 |
| WO | WO 96/26214 | 8/1996 |
| WO | WO 96/30534 | 10/1996 |
| WO | WO 96/40754 | 12/1996 |
| WO | WO 96/40955 | 12/1996 |
| WO | WO 97/11669 | 4/1997 |
| WO | WO 97/15597 | 5/1997 |
| WO | WO 97/20575 | 6/1997 |
| WO | WO 97/26535 | 7/1997 |
| WO | WO 97/29195 | 8/1997 |
| WO | WO 97/31017 | 8/1997 |
| WO | WO 97/34613 | 9/1997 |
| WO | WO 97/44475 | 11/1997 |
| WO | WO 97/47271 | 12/1997 |
| WO | WO 98/02538 | 1/1998 |
| WO | WO 98/04727 | 2/1998 |
| WO | WO 98/10780 | 3/1998 |
| WO | WO 98/14464 | 4/1998 |
| WO | WO 98/15636 | 4/1998 |
| WO | WO 98/17783 | 4/1998 |
| WO | WO 98/33810 | 8/1998 |
| WO | WO 98/58951 | 12/1998 |
| WO | WO 99/02183 | 1/1999 |
| WO | WO 99/19478 | 4/1999 |
| WO | WO 99/27101 | 6/1999 |
| WO | WO 99/30733 *  | 6/1999 |
| WO | WO 99 18206 | 8/1999 |
| WO | WO 99/40188 | 8/1999 |
| WO | WO 99/46992 | 9/1999 |
| WO | WO 99/50292 | 10/1999 |
| WO | WO 99/61034 | 12/1999 |
| WO | WO 01/30847 | 5/2001 |

OTHER PUBLICATIONS

Barnett et al. (1997) Vaccine, vol. 15 (8), 869-873.*
Lehner et al. (1999) J. Infect. Dis., vol. 179 (Suppl 3), S489-S492.*
Merriam-Webster Online Medical Dictionary. Definition of "subcutaneous". http://www2.merriam-webster.com/cgi-bin/mwmednlm?book=Medical&va=subcutaneous, (2011).*
Rao, V.S. et al., "Partial characterization of two subpopulations of T4 cells induced by active specific intralymphatic immunotherapy in melanoma patients", Proc. Amer. Assoc. Cancer Research Annual Meeting, vol. 27:325 (1986).
Nestle, Frank O., "Vaccination of melanoma patients with peptide-or tumor lysate-pulsed dendritic cells", Nature Medicine vol. 4:328-332 (1998).
Van der Bruggen, P., Science 254:1643 (1991).
Kawakami, at al., J Immunol 154:3961-3968 (1995).
Kawakami, et al. J Exp Med 180:347-352 (1994).
Castelli, at al., J Exp Med 181:363-368 (1995).
Wang, et al., J Exp. Med 186:1131-1140 (1996).
Wolfet, et al., Eur J Immunol 24:759-764 (1994).
Rogner, et al., Genomics 29:729-731 (1995).
Boel, et al., Immunity 2:167-175 (1995).
Van den Eynde, et al., J Exp Med 182:689-698 (1995).
Gaugler, et al. Immunogenetics 44:323-330 (1996).
Theobald, et al., Proc Natl Aced Sci USA 92:11993-11997 (1995).
Fisk, et al., J Exp Med 181:2109-2117 (1995).
Kwong, at al., J Nall Cancer Inst 85:982-990 (1995).
Jerome, et al., J Immunol 151:1654-1662 (1993).
Ioannides, et al, J Immunol 151:3693-3703 (1993).
Takahashi, et al., J Immunol 153:2102-2109 (1994).
Xue, et al., The Prostate 30:73-78 (1997).
Israeli, at al., Cancer Res 54:1807-1811 (1994).
Zaremba, S., et al., Cancer Research 57:4570-4577 (1997).
Tsang, K.T., et al., J Int Cancer Inst 87:982-990 (1995).
Valmori, D., et al., J Immunol 164:1125-1131 (2000).
Eura, M., et al., Clinical Cancer Research 6:979-986 (2000).
Heidecker, et al., J Immunol 164:6041.6045 (2000).
Tartaglia, et al., Virology 188:217 (1992).
Tartaglia, et al., J. Virol 67:2370 (1993b).
Taylor, J., et al., Virology 187:321 (1992).
Matlashewski, at al., EMBO J 3(13):3257-3262 (1984).
Zakut-Houri, et al., EMBO J 4(5):1251-1255(1985).
Cox, et al. Identification of a Peptide Recognized by Five Melanoma-Specific Human Cytotoxic T Cell Lines. Science, vol. 264: 716-719 (1994).
Hodge, et al. Diversified Prime and Boost Protocols Using Recombinant Vaccine Virus and Recombinant Non-Replicating Avian Pox Virus to Enhance T-Cell Immunity and Antitumor Responses. Vaccine, vol. 15, issue 6/7, pp. (1997).
Hurpin, et al. The Mode of Presentation and Route of Administration Are Critical for the Induction of Immune Responses to p53 and Antitumor Immunity. Vaccine, vol. 16, No. 2/3, pp. 208-215 (1998).
Irvine, et al. Recombinant Virus Vaccination Against "Self" Antigens Using Anchor-Fixed immunogens. Cancer Res., vol. 59: 2536-2540 (1999).
Kawakami, et al. Identification of a Human Melanoma Antigen Recognized by Tumor-Inflitrating Lymphocytes Associated with in vivo Tumor Rejection. Proc. Natl. Acad. Sci. USA, vol. 91, pp. 6458-6462 (1994).
Kundig, et al. Fibroblasts as Efficient Antigen-Presenting Cells in Lymphoid Organs. Science, vol. 268, pp. 1343-1347 (1995).
U.S. Appl. No. 09/693,755, Berinstein et al.
Lehner, et al. Targeted Lymph Node Immunization with Simian Immunodeficiency Virus p27 Antigen to Elicit Genital, Rectal, and Urinary Immune Responses in Nonhuman Primates. J. Immunol. vol. 153: 1858-1868 (1994).
Lehner, et al. Protective Mucosal Immunity Elicited by Targeted Iliac Lymph Node Immunization with a Subunit SIV Envelope and Core Vaccine in Macaques. Nat. Med. vol. 2, No. 7, pp. 767-775 (1996).
Lehner, et al. The Effect of Route of Immunization on Mucosal Immunity. J. Infect. Dis. 179(supp. 3), pp. S489-S492 (1999).
Mackensen, et al. Homing of Intravenously and Intralymphatically Injected Human Dendritic Cells Generated in vitro from CD34+ Hematopoictic Progenitor Cells. Cancer Immunol. Immunother. vol. 48, pp. 118-122 (1999).
Nestle, et al. Vaccination of Melanoma Patients with Peptide- or Tumor Lysate-Pulsed Dendritic Cells. Nature Med. vol. 4, No. 3, pp. 328-332 (1998).
Parkhurst, et al. Improved Induction of Melanoma-Reactive CTL with Peptides from Melanoma Antigen gp100 Modified at HLA-A0201-Binding Residues. J. Immunol. vol. 157, No. 6, pp. 2539-2548 (1996).
Pond, et al. Interactions Between Adipose Tissue Around Lymph Nodes and Lymphoid Cells in vitro. vol. 36. pp. 2219-2231 (1995).

Punt, et al. Biodistribution and Vaccine Efficiency of Murine Dendritic Cells are Dependent on the Route of Administration. Cancer Res. vol. 59, pp. 3340-3345 (1999).

Rao, et al. Partial Characterization of Two Subpopulations of T4 Cells Induced by Active Specific Intralymphatic Immunotherapy (ASILI) in Melanoma Patients, vol. 27, abstract 1290 (1986).

Restifo, et al. Antigen Processing in Vivo and the Elicitation of Primary CTL Responses. J. Immunol. 154: 4414-4422 (1995).

Salgaller, et al. Immunization Against Epitopes in the Human Melanoma Antigen gp100 Following Patient Immuniization with Synthetic Peptides, Cancer Res. vol. 56, pp. 4749-4757 (1996).

Wira, et al. Effect of Uterine Immunization and Oestradiol on Specific IgA and IgG Antibodies in Uterine, Vaginal and Salivary Secretions. Immunology, vol. 68, pp. 24-30 (1989).

Wira, et al. Specific IgA and IgG Antibodies in the Secretions of the Female Reproductive Tract: Effects of Immunization and Estradiol on Expression of this Response in vitro. J. Immunol. vol. 138, No. 12, pp. 4159-4164 (1987).

Wolfel, et al. Two Tyrosine Nonapeptides Recognized on HLA-A2 Melanomas by Autologous Cytolytic T Lymphocytes. Eur. J. Immunol. vol. 24, pp. 759-764 (1994).

Xiang, et al. An Autologous Oral DNA Vaccine Protects Against Murine Melanoma. Proc. Natl. Acad. Sci. USA, vol. 97, No. 10, pp. 5492-5497 (2000).

Zaremba, et al. Identification of an Enhancer Agonist Cytotoxic T Lymphocyte Peptide from Human Carcinoembryonic Antigen. Cancer Res. Vo. 57, pp. 4570-4577 (1997).

Hadzantonis, et al. Dendritic Cell lmmunotherapy for Melanoma. Cancer Blotherapy & Radiopharmaceuticals, 14:11-22 (1999).

Fintor, et al. Melanoma Vaccine Momentum Spurs Interest. Investment. J. Natl. Cancer Inst. 92: 1205-1207 (2000).

Ghose, et al. Immunogenecity of Whole-Cell Tumor Preparations Infected with the ALVAC Viral Vector. Human Gene Ther. 11: 1289-1301 (2000).

Timmerman, J.M. et al., "Melanoma vaccines: Prim and proper presentation", Nature Medicine vol. 4:269-270 (1998).

Mackensen, Andreas et al., "Homing of intravenously and intralymphatically injected human dendritic cells generated In vitro from CD34+ hematopoietic progenitor cells", Cancer Immunology Immunotherapy, vol. 48:118-122 (1999).

Irvine, Kari R. et al., "Recombinant Virus Vaccination against "Self" Antigens Using Anchor-fixed Immunogens", Cancer Research vol. 59:2536-2540 (1999).

Plotkin, Stanley A., "General Immunization Practices", Vaccines Chapter 5, 47-73 (1999).

Sigel, M. B. et al., "Production of Antibodies by Inoculation into Lymph Nodes", Methods in Enzymology vol. 93:3-13, (1983).

Horig, H. et al., "Short Analytical Review: Current Issues in Cancer Vaccine Development" Clinical Immunology vol. 92, No. 3 pp. 211-223 (1999).

* cited by examiner

Monkey #6 (Intranodal Administration)

Monkey # 11 (Subcutaneous Administration)

Monkey #10 (Subcutaneous Administration)

FIGURE 6

```
                ATGG ATCTGGTGCT AAAAAGATGC CTTCTTCATT TGGCTGTGAT
AGGTGCTTTG CTGGCTGTGG GGGCTACAAA AGTACCCAGA AACCAGGACT GGCTTGGTGT
CTCAAGGCAA CTCAGAACCA AAGCCTGGAA CAGGCAGCTG TATCCAGAGT GGACAGAAGC
CCAGAGACTT GACTGCTGGA GAGGTGGTCA AGTGTCCCTC AAGGTCAGTA ATGATGGGCC
TACACTGATT GGTGCAAATG CCTCCTTCTC TATTGCCTTG AACTTCCCTG GAAGCCAAAA
GGTATTGCCA GATGGGCAGG TTATCTGGGT CAACAATACC ATCATCAATG GGAGCCAGGT
GTGGGCAGGA CAGCCAGTGT ATCCCCAGGA AACTGACGAT GCCTGCATCT TCCCTGATGG
TGGACCTTGC CCATCTGGCT CTTGGTCTCA GAAGAGAAGC TTTGTTTATG TCTGGAAGAC
CTGGGGCCAA TACTGGCAAG TTCTAGGGGG CCCAGTGTCT GGGCTGAGCA TTGGGACAGG
CAGGGCAATG CTGGGCACAC ACACGATGGA AGTGACTGTC TACCATCGCC GGGGATCCCG
GAGCTATGTG CCTCTTGCTC ATTCCAGCTC AGCCTTCACC ATTATGGACC AGGTGCCTTT
CTCCGTGAGC GTGTCCCAGT TGCGGGCCTT GGATGGAGGG AACAAGCACT TCCTGAGAAA
TCAGCCTCTG ACCTTTGCCC TCCAGCTCCA TGACCCCAGT GGCTATCTGG CTGAAGCTGA
CCTCTCCTAC ACCTGGGACT TTGGAGACAG TAGTGGAACC CTGATCTCTC GGGCACTTGT
GGTCACTCAT ACTTACCTGG AGCCTGGCCC AGTCACTGTT CAGGTGGTCC TGCAGGCTGC
CATTCCTCTC ACCTCCTGTG GCTCCTCCCC AGTTCCAGGC ACCACAGATG GGCACAGGCC
AACTGCAGAG GCCCCTAACA CCACAGCTGG CCAAGTGCCT ACTACAGAAG TTGTGGGTAC
TACACCTGGT CAGGCGCCAA CTGCAGAGCC CTCTGGAACC ACATCTGTGC AGGTGCCAAC
CACTGAAGTC ATAAGCACTG CACCTGTGCA GATGCCAACT GCAGAGAGCA CAGGTATGAC
ACCTGAGAAG GTGCCAGTTT CAGAGGTCAT GGGTACCACA CTGGCAGAGA TGTCAACTCC
AGAGGCTACA GGTATGACAC CTGCAGAGGT ATCAATTGTG GTGCTTTCTG GAACCACAGC
TGCACAGGTA ACAACTACAG AGTGGGTGGA GACCACAGCT AGAGAGCTAC CTATCCCTGA
GCCTGAAGGT CCAGATGCCA GCTCAATCAT GTCTACGGAA AGTATTACAG GTTCCCTGGG
CCCCCTGCTG GATGGTACAG CCACCTTAAG GCTGGTGAAG AGACAAGTCC CCTGGATTG
TGTTCTGTAT CGATATGGTT CCTTTTCCGT CACCCTGGAC ATTGTCCAGG GTATTGAAAG
TGCCGAGATC CTGCAGGCTG TGCCGTCCGG TGAGGGGGAT GCATTTGAGC TGACTGTGTC
CTGCCAAGGC GGGCTGCCCA AGGAAGCCTG CATGGAGATC TCATCGCCAG GGTGCCAGCC
CCCTGCCCAG CGGCTGTGCC AGCCTGTGCT ACCAGCCCA GCCTGCCAGC TGGTTCTGCA
CCAGATACTG AAGGGTGGCT CGGGGACATA CTGCCTCAAT GTGTCTCTGG CTGATACCAA
CAGCCTGGCA GTGGTCAGCA CCCAGCTTAT CATGCCTGGT CAAGAAGCAG GCCTTGGGCA
GGTTCCGCTG ATCGTGGGCA TCTTGCTGGT GTTGATGGCT GTGGTCCTTG CATCTCTGAT
ATATAGGCGC AGACTTATGA AGCAAGACTT CTCCGTACCC CAGTTGCCAC ATAGCAGCAG
TCACTGGCTG CGTCTACCCC GCATCTTCTG CTCTTGTCCC ATTGGTGAGA ACAGCCCCT
CCTCAGTGGG CAGCAGGTCT GA
```

FIGURE 7

Met Asp Leu Val Leu Lys Arg Cys Leu Leu His Leu Ala Val Ile Gly
1                  5                      10                     15

Ala Leu Leu Ala Val Gly Ala Thr Lys Val Pro Arg Asn Gln Asp Trp
                20                      25                     30

Leu Gly Val Ser Arg Gln Leu Arg Thr Lys Ala Trp Asn Arg Gln Leu
            35                      40                     45

Tyr Pro Glu Trp Thr Glu Ala Gln Arg Leu Asp Cys Trp Arg Gly Gly
        50                      55                     60

Gln Val Ser Leu Lys Val Ser Asn Asp Gly Pro Thr Leu Ile Gly Ala
65                      70                      75                 80

Asn Ala Ser Phe Ser Ile Ala Leu Asn Phe Pro Gly Ser Gln Lys Val
                85                      90                     95

Leu Pro Asp Gly Gln Val Ile Trp Val Asn Asn Thr Ile Ile Asn Gly
            100                     105                    110

Ser Gln Val Trp Gly Gly Gln Pro Val Tyr Pro Gln Glu Thr Asp Asp
            115                     120                    125

Ala Cys Ile Phe Pro Asp Gly Gly Pro Cys Pro Ser Gly Ser Trp Ser
        130                     135                    140

Gln Lys Arg Ser Phe Val Tyr Val Trp Lys Thr Trp Gly Gln Tyr Trp
145                     150                     155                160

Gln Val Leu Gly Gly Pro Val Ser Gly Leu Ser Ile Gly Thr Gly Arg
                165                     170                    175

Ala Met Leu Gly Thr His Thr Met Glu Val Thr Val Tyr His Arg Arg
            180                     185                    190

Gly Ser Arg Ser Tyr Val Pro Leu Ala His Ser Ser Ser Ala Phe Thr
        195                     200                    205

Met
Ile Ser Asp Gln Val Pro Phe Ser Val Ser Val Ser Gln Leu Arg Ala
    210                     215                    220

Leu Asp Gly Gly Asn Lys His Phe Leu Arg Asn Gln Pro Leu Thr Phe
225                     230                     235                240

Ala Leu Gln Leu His Asp Pro Ser Gly Tyr Leu Ala Glu Ala Asp Leu
            245                     250                    255

Ser Tyr Thr Trp Asp Phe Gly Asp Ser Ser Gly Thr Leu Ile Ser Arg
            260                     265                    270
                                                               Val
Ala Leu Val Val Thr His Thr Tyr Leu Glu Pro Gly Pro Val Thr
        275                     280                     285

Gln Val Val Leu Gln Ala Ala Ile Pro Leu Thr Ser Cys Gly Ser Ser
290                     295                     300

Pro Val Pro Gly Thr Thr Asp Gly His Arg Pro Thr Ala Glu Ala Pro
305                     310                     315                320

Asn Thr Thr Ala Gly Gln Val Pro Thr Thr Glu Val Val Gly Thr Thr
                325                     330                    335

Pro Gly Gln Ala Pro Thr Ala Glu Pro Ser Gly Thr Thr Ser Val Gln
            340                     345                    350

Val Pro Thr Thr Glu Val Ile Ser Thr Ala Pro Val Gln Met Pro Thr
        355                     360                    365

FIGURE 7 (CONT'D)

```
Ala Glu Ser Thr Gly Met Thr Pro Glu Lys Val Pro Val Ser Glu Val
    370             375             380
Met Gly Thr Thr Leu Ala Glu Met Ser Thr Pro Glu Ala Thr Gly Met
385             390             395                         400
Thr Pro Ala Glu Val Ser Ile Val Val Leu Ser Gly Thr Thr Ala Ala
            405                 410                     415
Gln Val Thr Thr Thr Glu Trp Val Glu Thr Thr Ala Arg Glu Leu Pro
            420                 425                 430
Ile Pro Glu Pro Glu Gly Pro Asp Ala Ser Ser Ile Met Ser Thr Glu
        435             440                 445
Ser Ile Thr Gly Ser Leu Gly Pro Leu Leu Asp Gly Thr Ala Thr Leu
    450             455                 460
Arg Leu Val Lys Arg Gln Val Pro Leu Asp Cys Val Leu Tyr Arg Tyr
465             470             475                     480
Gly Ser Phe Ser Val Thr Leu Asp Ile Val Gln Gly Ile Glu Ser Ala
                485                 490                 495
Glu Ile Leu Gln Ala Val Pro Ser Gly Glu Gly Asp Ala Phe Glu Leu
                500             505             510
Thr Val Ser Cys Gln Gly Gly Leu Pro Lys Glu Ala Cys Met Glu Ile
            515             520             525
Ser Ser Pro Gly Cys Gln Pro Pro Ala Gln Arg Leu Cys Gln Pro Val
    530             535             540
Leu Pro Ser Pro Ala Cys Gln Leu Val Leu His Gln Ile Leu Lys Gly
545             550             555                     560
Gly Ser Gly Thr Tyr Cys Leu Asn Val Ser Leu Ala Asp Thr Asn Ser
                565             570                 575
Leu Ala Val Val Ser Thr Gln Leu Ile Met Pro Gly Gln Glu Ala Gly
            580             585             590
Leu Gly Gln Val Pro Leu Ile Val Gly Ile Leu Leu Val Leu Met Ala
        595             600                 605
Val Val Leu Ala Ser Leu Ile Tyr Arg Arg Arg Leu Met Lys Gln Asp
610             615             620
Phe Ser Val Pro Gln Leu Pro His Ser Ser Ser His Trp Leu Arg Leu
625             630             635                     640
Pro Arg Ile Phe Cys Ser Cys Pro Ile Gly Glu Asn Ser Pro Leu Leu
                645             650                 655
Ser Gly Gln Gln Val
            660
```

```
      ATGGAGTCTCCCTCGGCCCCTCCCCACAGATGGTGCATCCCCTGGCAGAGGCTCCTGCTC
    1 ---------+---------+---------+---------+---------+---------+ 60
      TACCTCAGAGGGAGCCGGGGAGGGGTGTCTACCACGTAGGGGACCGTCTCCGAGGACGAG a     M   E   S   P   S   A   P   P   H   R   W   C   I   P   W   Q   R   L   L   L   -

ACAGCCTCACTTCTAACCTTCTGGAACCCGCCCACCACTGCCAAGCTCACTATTGAATCC
   61 ---------+---------+---------+---------+---------+---------+ 120
      TGTCGGAGTGAAGATTGGAAGACCTTGGGCGGGTGGTGACGGTTCGAGTGATAACTTAGG a     T   A   S   L   L   T   F   W   N   P   P   T   T   A   K   L   T   I   E   S   -

ACGCCGTTCAATGTCGCAGAGGGGAAGGAGGTGCTTCTACTTGTCCACAATCTGCCCCAG
  121 ---------+---------+---------+---------+---------+---------+ 180
      TGCGGCAAGTTACAGCGTCTCCCCTTCCTCCACGAAGATGAACAGGTGTTAGACGGGGTC a     T   P   F   N   V   A   E   G   K   E   V   L   L   L   V   H   N   L   P   Q   -

CATCTTTTTGGCTACAGCTGGTACAAAGGTGAAAGAGTGGATGGCAACCGTCAAATTATA
  181 ---------+---------+---------+---------+---------+---------+ 240
      GTAGAAAAACCGATGTCGACCATGTTTCCACTTTCTCACCTACCGTTGGCAGTTTAATAT a     H   L   F   G   Y   S   W   Y   K   G   E   R   V   D   G   N   R   Q   I   I   -

GGATATGTAATAGGAACTCAACAAGCTACCCCAGGGCCCGCATACAGTGGTCGAGAGATA
  241 ---------+---------+---------+---------+---------+---------+ 300
      CCTATACATTATCCTTGAGTTGTTCGATGGGGTCCCGGGCGTATGTCACCAGCTCTCTAT a     G   Y   V   I   G   T   Q   Q   A   T   P   G   P   A   Y   S   G   R   E   I   -

ATATACCCCAATGCATCCCTGCTGATCCAGAACATCATCCAGAATGACACAGGATTCTAC
  301 ---------+---------+---------+---------+---------+---------+ 360
      TATATGGGGTTACGTAGGGACGACTAGGTCTTGTAGTAGGTCTTACTGTGTCCTAAGATG a     I   Y   P   N   A   S   L   L   I   Q   N   I   I   Q   N   D   T   G   F   Y   -

ACCCTACACGTCATAAAGTCAGATCTTGTGAATGAAGAAGCAACTGGCCAGTTCCGGGTA
  361 ---------+---------+---------+---------+---------+---------+ 420
      TGGGATGTGCAGTATTTCAGTCTAGAACACTTACTTCTTCGTTGACCGGTCAAGGCCCAT a     T   L   H   V   I   K   S   D   L   V   N   E   E   A   T   G   Q   F   R   V   -

TACCCGGAGCTGCCCAAGCCCTCCATCTCCAGCAACAACTCCAAACCCGTGGAGGACAAG
  421 ---------+---------+---------+---------+---------+---------+ 480
      ATGGGCCTCGACGGGTTCGGGAGGTAGAGGTCGTTGTTGAGGTTTGGGCACCTCCTGTTC a     Y   P   E   L   P   K   P   S   I   S   S   N   N   S   K   P   V   E   D   K   -

GATGCTGTGGCCTTCACCTGTGAACCTGAGACTCAGGACGCAACCTACCTGTGGTGGGTA
  481 ---------+---------+---------+---------+---------+---------+ 540
      CTACGACACCGGAAGTGGACACTTGGACTCTGAGTCCTGCGTTGGATGGACACCACCCAT a     D   A   V   A   F   T   C   E   P   E   T   Q   D   A   T   Y   L   W   W   V   -

AACAATCAGAGCCTCCCCGGTCAGTCCCAGGCTGCAGCTGTCCAATGGCAACAGGACCCTC
  541 ---------+---------+---------+---------+---------+---------+ 600
      TTGTTAGTCTCGGAGGGCCAGTCAGGGTCCGACGTCGACAGGTTACCGTTGTCCTGGGAG a     N   N   Q   S   L   P   V   S   P   R   L   Q   L   S   N   G   N   R   T   L   -

ACTCTATTCAATGTCACAAGAAATGACACAGCAAGCTACAAATGTGAAACCCAGAACCCA
  601 ---------+---------+---------+---------+---------+---------+ 660
      TGAGATAAGTTACAGTGTTCTTTACTGTGTCGTTCGATGTTTACACTTTGGGTCTTGGGT a     T   L   F   N   V   T   R   N   D   T   A   S   Y   K   C   E   T   Q   N   P   -

GTGAGTGCCAGGCGCAGTGATTCAGTCATCCTGAATGTCCTCTATGGCCCGGATGCCCCC
  661 ---------+---------+---------+---------+---------+---------+ 720
      CACTCACGGTCCGCGTCACTAAGTCAGTAGGACTTACAGGAGATACCGGGCCTACGGGGG a     V   S   A   R   R   S   D   S   V   I   L   N   V   L   Y   G   P   D   A   P   -
```

Figure 8

```
          ACCATTTCCCCTCTAAACACATCTTACAGATCAGGGGAAAATCTGAACCTCTCCTGCCAC
      721 ---------+---------+---------+---------+---------+---------+ 780
          TGGTAAAGGGGAGATTTGTGTAGAATGTCTAGTCCCCTTTTAGACTTGGAGAGGACGGTG a     T  I  S  P  L  N  T  S  Y  R  S  G  E  N  L  N  L  S  C  H   -

GCAGCCTCTAACCCACCTGCACAGTACTCTTGGTTTGTCAATGGGACTTTCCAGCAATCC
      781 ---------+---------+---------+---------+---------+---------+ 840
          CGTCGGAGATTGGGTGGACGTGTCATGAGAACCAAACAGTTACCCTGAAAGGTCGTTAGG a     A  A  S  N  P  P  A  Q  Y  S  W  F  V  N  G  T  F  Q  Q  S   -

ACCCAAGAGCTCTTTATCCCCAACATCACTGTGAATAATAGTGGATCCTATACGTGCCAA
      841 ---------+---------+---------+---------+---------+---------+ 900
          TGGGTTCTCGAGAAATAGGGGTTGTAGTGACACTTATTATCACCTAGGATATGCACGGTT a     T  Q  E  L  F  I  P  N  I  T  V  N  N  S  G  S  Y  T  C  Q   -

GCCCATAACTCAGACACTGGCCTCAATAGGACCACAGTCACGACGATCACAGTCTATGAG
      901 ---------+---------+---------+---------+---------+---------+ 960
          CGGGTATTGAGTCTGTGACCGGAGTTATCCTGGTGTCAGTGCTGCTAGTGTCAGATACTC a     A  H  N  S  D  T  G  L  N  R  T  T  V  T  T  I  T  V  Y  E   -

CCACCCAAACCCTTCATCACCAGCAACAACTCCAACCCCGTGGAGGATGAGGATGCTGTA
      961 ---------+---------+---------+---------+---------+---------+ 1020
          GGTGGGTTTGGGAAGTAGTGGTCGTTGTTGAGGTTGGGGCACCTCCTACTCCTACGACAT a     P  P  K  P  F  I  T  S  N  N  S  N  P  V  E  D  E  D  A  V   -

GCCTTAACCTGTGAACCTGAGATTCAGAACACAACCTACCTGTGGTGGGTAAATAATCAG
     1021 ---------+---------+---------+---------+---------+---------+ 1080
          CGGAATTGGACACTTGGACTCTAAGTCTTGTGTTGGATGGACACCACCCATTTATTAGTC a     A  L  T  C  E  P  E  I  Q  N  T  T  Y  L  W  W  V  N  N  Q   -

AGCCTCCCGGTCAGTCCCAGGCTGCAGCTGTCCAATGACAACAGGACCCTCACTCTACTC
     1081 ---------+---------+---------+---------+---------+---------+ 1140
          TCGGAGGGCCAGTCAGGGTCCGACGTCGACAGGTTACTGTTGTCCTGGGAGTGAGATGAG a     S  L  P  V  S  P  R  L  Q  L  S  N  D  N  R  T  L  T  L  L   -

AGTGTCACAAGGAATGATGTAGGACCCTATGAGTGTGGAATCCAGAACGAATTAAGTGTT
     1141 ---------+---------+---------+---------+---------+---------+ 1200
          TCACAGTGTTCCTTACTACATCCTGGGATACTCACACCTTAGGTCTTGCTTAATTCACAA a     S  V  T  R  N  D  V  G  P  Y  E  C  G  I  Q  N  E  L  S  V   -

GACCACAGCGACCCAGTCATCCTGAATGTCCTCTATGGCCCAGACGACCCCACCATTTCC
     1201 ---------+---------+---------+---------+---------+---------+ 1260
          CTGGTGTCGCTGGGTCAGTAGGACTTACAGGAGATACCGGGTCTGCTGGGGTGGTAAAGG a     D  H  S  D  P  V  I  L  N  V  L  Y  G  P  D  D  P  T  I  S   -

CCCTCATACACCTATTACCGTCCAGGGGTGAACCTCAGCCTCTCCTGCCATGCAGCCTCT
     1261 ---------+---------+---------+---------+---------+---------+ 1320
          GGGAGTATGTGGATAATGGCAGGTCCCCACTTGGAGTCGGAGAGGACGGTACGTCGGAGA a     P  S  Y  T  Y  Y  R  P  G  V  N  L  S  L  S  C  H  A  A  S   -

AACCCACCTGCACAGTATTCTTGGCTGATTGATGGGAACATCCAGCAACACACACAAGAG
     1321 ---------+---------+---------+---------+---------+---------+ 1380
          TTGGGTGGACGTGTCATAAGAACCGACTAACTACCCTTGTAGGTCGTTGTGTGTGTTCTC a     N  P  P  A  Q  Y  S  W  L  I  D  G  N  I  Q  Q  H  T  Q  E   -

CTCTTTATCTCCAACATCACTGAGAAGAACAGCGGACTCTATACCTGCCAGGCCAATAAC
     1381 ---------+---------+---------+---------+---------+---------+ 1440
          GAGAAATAGAGGTTGTAGTGACTCTTCTTGTCGCCTGAGATATGGACGGTCCGGTTATTG a     L  F  I  S  N  I  T  E  K  N  S  G  L  Y  T  C  Q  A  N  N   -
```

Figure 8, con't

```
        TCAGCCAGTGGCCACAGCAGGACTACAGTCAAGACAATCACAGTCTCTGCGGAGCTGCCC
   1441 ---------+---------+---------+---------+---------+---------+ 1500
        AGTCGGTCACCGGTGTCGTCCTGATGTCAGTTCTGTTAGTGTCAGAGACGCCTCGACGGG a       S  A  S  G  H  S  R  T  T  V  K  T  I  T  V  S  A  E  L  P   -

AAGCCCTCCATCTCCAGCAACAACTCCAAACCCGTGGAGGACAAGGATGCTGTGGCCTTC
   1501 ---------+---------+---------+---------+---------+---------+ 1560
        TTCGGGAGGTAGAGGTCGTTGTTGAGGTTTGGGCACCTCCTGTTCCTACGACACCGGAAG a       K  P  S  I  S  S  N  N  S  K  P  V  E  D  K  D  A  V  A  F   -

ACCTGTGAACCTGAGGCTCAGAACACAACCTACCTGTGGTGGGTAAATGGTCAGAGCCTC
   1561 ---------+---------+---------+---------+---------+---------+ 1620
        TGGACACTTGGACTCCGAGTCTTGTGTTGGATGGACACCACCCATTTACCAGTCTCGGAG a       T  C  E  P  E  A  Q  N  T  T  Y  L  W  W  V  N  G  Q  S  L   -

CCAGTCAGTCCCAGGCTGCAGCTGTCCAATGGCAACAGGACCCTCACTCTATTCAATGTC
   1621 ---------+---------+---------+---------+---------+---------+ 1680
        GGTCAGTCAGGGTCCGACGTCGACAGGTTACCGTTGTCCTGGGAGTGAGATAAGTTACAG a       P  V  S  P  R  L  Q  L  S  N  G  N  R  T  L  T  L  F  N  V   -

ACAAGAAATGACGCAAGAGCCTATGTATGTGGAATCCAGAACTCAGTGAGTGCAAACCGC
   1681 ---------+---------+---------+---------+---------+---------+ 1740
        TGTTCTTTACTGCGTTCTCGGATACATACACCTTAGGTCTTGAGTCACTCACGTTTGGCG a       T  R  N  D  A  R  A  Y  V  C  G  I  Q  N  S  V  S  A  N  R   -

AGTGACCCAGTCACCCTGGATGTCCTCTATGGGCCGGACACCCCCATCATTTCCCCCCCA
   1741 ---------+---------+---------+---------+---------+---------+ 1800
        TCACTGGGTCAGTGGGACCTACAGGAGATACCCGGCCTGTGGGGGTAGTAAAGGGGGGGT a       S  D  P  V  T  L  D  V  L  Y  G  P  D  T  P  I  I  S  P  P   -

GACTCGTCTTACCTTTCGGGAGCGGACCTCAACCTCTCCTGCCACTCGGCCTCTAACCCA
   1801 ---------+---------+---------+---------+---------+---------+ 1860
        CTGAGCAGAATGGAAAGCCCTCGCCTGGAGTTGGAGAGGACGGTGAGCCGGAGATTGGGT a       D  S  S  Y  L  S  G  A  D  L  N  L  S  C  H  S  A  S  N  P   -

TCCCCGCAGTATTCTTGGCGTATCAATGGGATACCGCAGCAACACACACAAGTTCTCTTT
   1861 ---------+---------+---------+---------+---------+---------+ 1920
        AGGGGCGTCATAAGAACCGCATAGTTACCCTATGGCGTCGTTGTGTGTGTTCAAGAGAAA a       S  P  Q  Y  S  W  R  I  N  G  I  P  Q  Q  H  T  Q  V  L  F   -

ATCGCCAAAATCACGCCAAATAATAACGGGACCTATGCCTGTTTTGTCTCTAACTTGGCT
   1921 ---------+---------+---------+---------+---------+---------+ 1980
        TAGCGGTTTTAGTGCGGTTTATTATTGCCCTGGATACGGACAAAACAGAGATTGAACCGA a       I  A  K  I  T  P  N  N  G  T  Y  A  C  F  V  S  N  L  A   -

ACTGGCCGCAATAATTCCATAGTCAAGAGCATCACAGTCTCTGCATCTGGAACTTCTCCT
   1981 ---------+---------+---------+---------+---------+---------+ 2040
        TGACCGGCGTTATTAAGGTATCAGTTCTCGTAGTGTCAGAGACGTAGACCTTGAAGAGGA a       T  G  R  N  N  S  I  V  K  S  I  T  V  S  A  S  G  T  S  P   -

GGTCTCTCAGCTGGGGCCACTGTCGGCATCATGATTGGAGTGCTGGTTGGGGTTGCTCTG
   2041 ---------+---------+---------+---------+---------+---------+ 2100
        CCAGAGAGTCGACCCCGGTGACAGCCGTAGTACTAACCTCACGACCAACCCCAACGAGAC a       G  L  S  A  G  A  T  V  G  I  M  I  G  V  L  V  G  V  A  L   -

ATATAG ←
   2101 ------ 2106
        TATATC a       I  * ←
```

Figure 8, con't

METHOD OF INDUCING AND/OR ENHANCING AN IMMUNE RESPONSE TO TUMOR ANTIGENS

This application claims the benefit of U.S. application Ser. No. 60/160,879, filed on Oct. 22, 1999 and U.S. application Ser. No. 60/223,325 filed on Aug. 7, 2000, both of which are incorporated by reference herein.

FIELD OF THE INVENTION

The present invention relates to methods for inducing and/or enhancing immune responses to tumor antigens.

BACKGROUND OF THE INVENTION

Using immunological approaches to cancer therapy has been difficult as tumor cells are self-derived and therefore not as immunogenic as exogenous agents such as bacteria and viruses. As a result, the prospects of cancer immunotherapy rely upon the identification of tumor associated antigens ("TAA") which can be recognized by the immune system. Specifically, target antigens eliciting T cell-mediated responses are of critical interest. This comes from evidence that cytotoxic T lymphocytes (CTLs) can induce tumor regression both in animal models (Kast W. et al (1989) *Cell* 59:6035; Greendberg. P. (1991) *Adv. Immunol.* 49:281) and in humans (soon T. et al. (1994) *Anna. Rev. Immunol.* 12:337). To date, many tumor associated antigens have been identified. These include the antigens MAGE, BAGE, GAGE, RAGE, gp100, MART-1/Melan-A, tyrosinase, carcinoembryonic antigen (CEA) as well as many others (Hong and Kaufman (1999) *Clinical Immunology* 92:211-223). Some of these tumor associated antigens are discussed below.

The first human tumor associated antigen characterized was identified from a melanoma. This antigen (originally designated MAGE 1) was identified using CTLs isolated from an HLA A1+ melanoma patient to screen HLA A1 target cells transfected with tumor DNA (van der Bruggen P. (1991) *Science*, 254:1643; these tumor associated antigens are now designated MAGE-A1, MAGE-A2, etc.). Interestingly, MAGE 1 was found to belong to a family of at least 12 closely related genes located on the X chromosome (de Plaen, E. et al. (1994) *Immunogenetics* 40:360). The nucleic acid sequence of the 11 additional MAGE genes share 65-85% identity with that of MAGE-1 (de Smet, C. at al. (1994) *Immunogenetics* 39:121). Both MAGE 1 and 3 are present in normal tissues, but expressed only in the testis (de Plaen, E. et al. (1994) Supra; de Smet, C. et al. (1994) Supra; Takahashi, K. et al. (1995) *Cancer Res.* 55:3478; Chyomey, P. et al. (1995) *Immunogenetics* 43:97). These initial results have subsequently been extended with the identification of new gene families (i.e. RAGE, BAGE, GAGE), all of which are typically not expressed in normal tissues (except testis) but expressed in a variety of tumor types.

Human carcinoembryonic antigen (CEA) is a 180 kD glycoprotein expressed on the majority of colon, rectal, stomach and pancreatic tumors (Muaro et al. (1985) *Cancer Res.* 45:5769), some 50% of breast carcinomas (Steward at al. (1974) *Cancer* 33-1246) and 70% of lung carcinomas (Vincent, R. G. and Chu, T. M. (1978) *J. Thor. Cardiovas. Surg.* 66:320). CEA was first described as a cancer specific fetal antigen in adenocarcinoma of the human digestive tract in 1965 (Gold, P. and Freeman, S. O. (1965) *Exp. Med.* 121.439). Since that time, CEA has been characterized as a cell surface antigen produced in excess in nearly all solid tumors of the human gastrointestinal tract. The gene for the human CEA protein has been cloned (Oikawa et at (1987) *Biochim. Biophys. Res.* 142.511-518; European Application No. EP 0346710). CEA is also expressed in fetal gut tissue and to a lesser extent on normal colon epithelium. The immunogenicity of CEA has been ambiguous, with several studies reporting the presence of anti-CEA antibodies in patients (Gold et al. (1973) *Nature New Biology* 239:60; Pompecki. R. (1980) *Eur. J. Cancer* 16:973; Ura et al (1985) *Cancer Lett.* 25:283; Fuchs et al. (1988) *Cancer Immunol. Immunother* 26:180) while other studies have not (LoGerfo et al. (1972) *Int. J. Cancer* 9:344; MacSween, J. M. (1975) *Int. J. Cancer* 15.246: Chester K. A. and Begent, H. J. (1984) *Clin. Exp. Immunol.* 58:685).

Gp100 is normally found in melanosomes and expressed in melanocytes, retinal cells, and other neural crest derivatives. The function of gp100 is currently unknown. By mass spectrometry, three immunodominant HLA-A2 binding gp100 epitopes have been identified: g9-154 (amino acids 154-162), g9-209 (amino acids 209-217); and g9-280 (amino acids 280-288). Notably, two of these epitopes (as peptides) have been synthetically altered so as to induce a more vigorous immune response in the original T cell clone: the threonine at position 2 in gp-209 was changed to a methionine, and the alanine residue at position 9 in gp-280 was changed to a valine These changes increase the binding affinity of the epitope-peptides to the HLA-A2 molecule without changing the intrinsic natural epitopes recognized by the T cell receptor (TCR). Rosenberg and colleagues (NIH) have already successfully immunized melanoma patients with one of these modified peptides and have reported achieving objective clinical responses in some patients.

Despite significant advances that have been made with respect to immunological approaches to cancer treatment, there is still a need in the art to improve cancer immunotherapies.

SUMMARY OF THE INVENTION

The present invention relates to improved methods for inducing and/or enhancing an immune response to a tumor antigen.

The present inventors have found that administering the tumor antigen or nucleic acid coding therefor directly into a lymphatic site (such as a lymph node) induces and/or significantly enhances the immune response to the tumor antigen and/or breaks tolerance to the tumor antigen, both which have been a major challenge in previous methods of cancer immunotherapy.

Accordingly, one aspect the present invention provides a method for inducing and/or enhancing an immune response in an animal to a tumor antigen comprising administering an effective amount of a tumor antigen, nucleic acid coding therefor, vector or cell comprising said nucleic acid, or vaccine comprising the aforementioned to a lymphatic site in the animal.

In another aspect, the present invention provides a method for breaking immune tolerance to a tumor antigen in an animal comprising administering an effective amount of a tumor antigen, nucleic acid coding therefor, vector or cell comprising said nucleic acid, or vaccine comprising the aforementioned to a lymphatic site in the animal.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 6 is the nucleic acid sequence of a modified gp100M cDNA (SEQ.ID.NO.:109).

FIG. 7 is the deduced amino acid sequence of the modified gp100M protein (SEQ.ID.NO.:110)

FIG. 8 is the nucleic acid and amino acid sequence of a modified CEA (SEQ.ID.NOS.: 111 and 112).

DETAILED DESCRIPTION OF THE INVENTION

Figure 1:
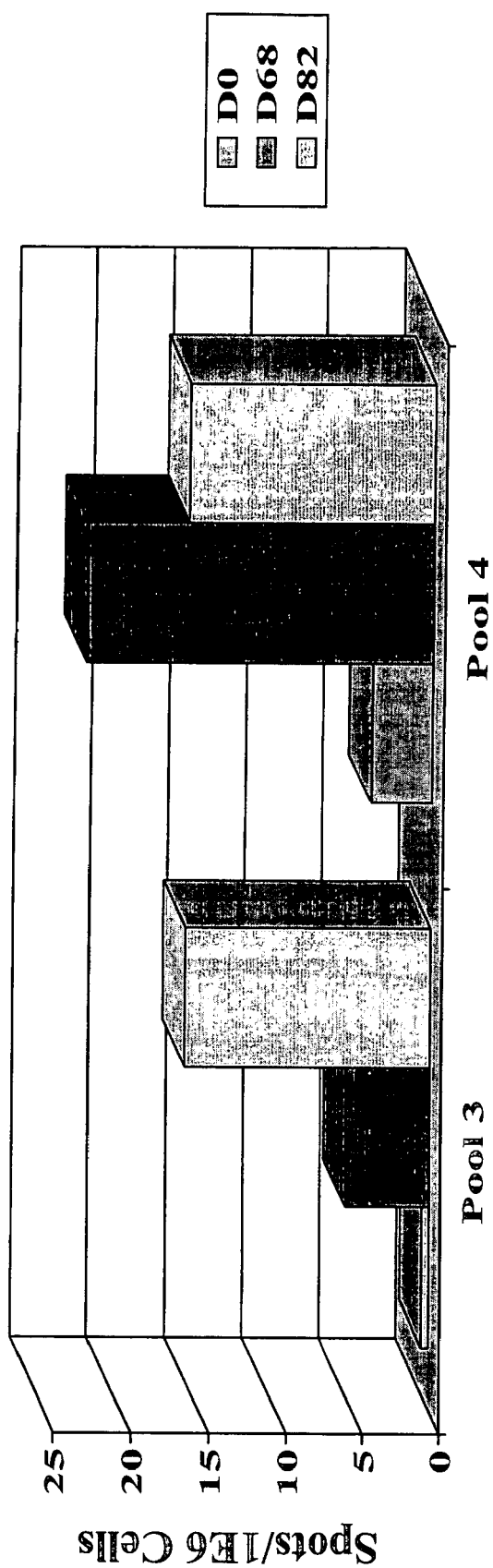
FIG. 1 is a bar graph showing the results of an IFN-γ-ELISPOT analysis of an animal receiving an intranodal injection of the tumor antigen
Figure 2:
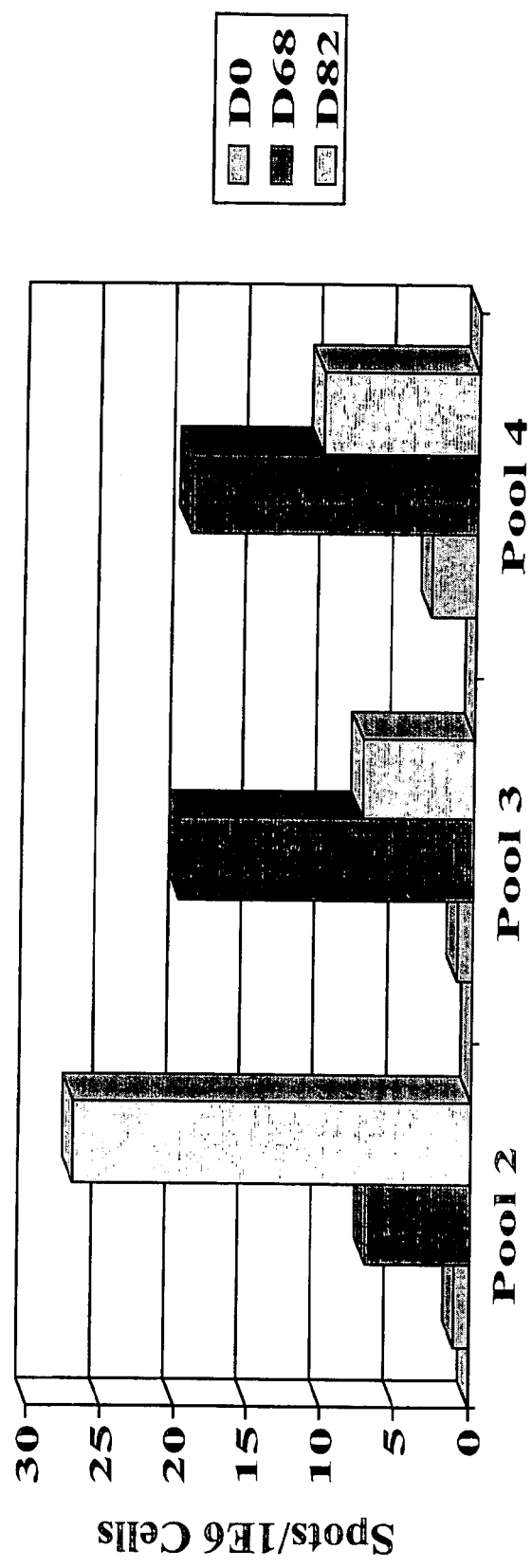
FIG. 2 is a bar graph showing the results of an IFN-γ-ELISPOT analysis of an animal receiving an intranodal injection of the tumor antigen
Figure 3:
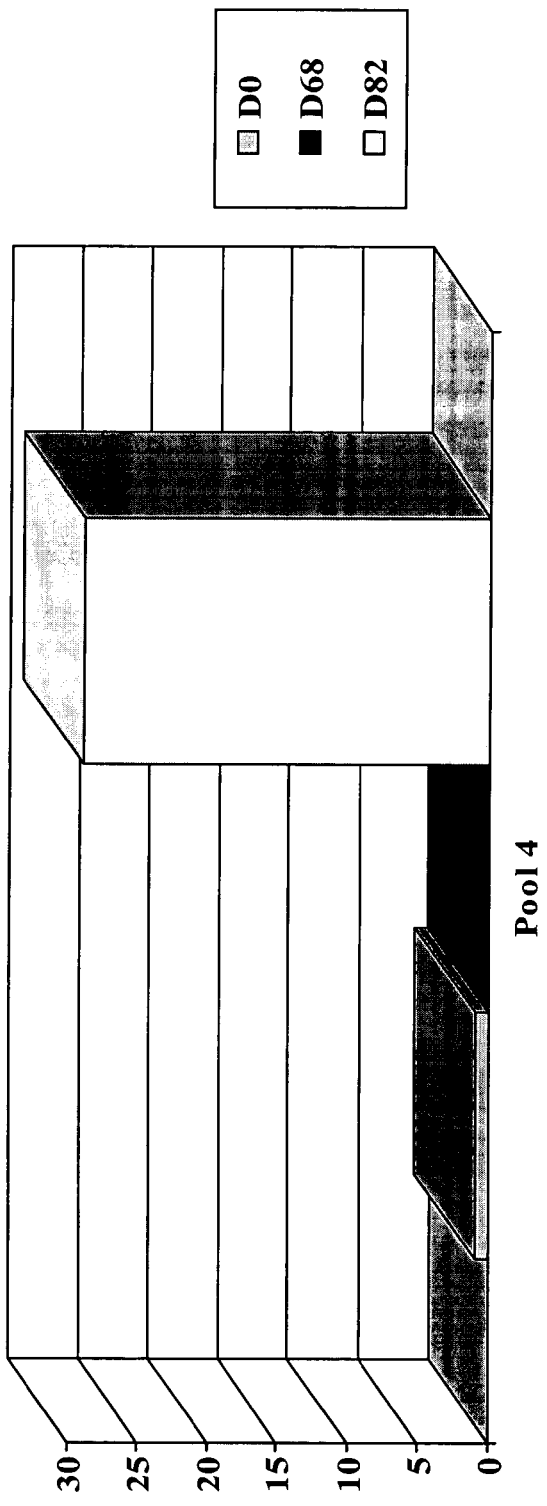
FIG. 3 is a bar graph showing the results of an IFN-γ-ELISPOT analysis of an animal receiving a subcutaneous injection of the tumor antigen.
Figure 4:
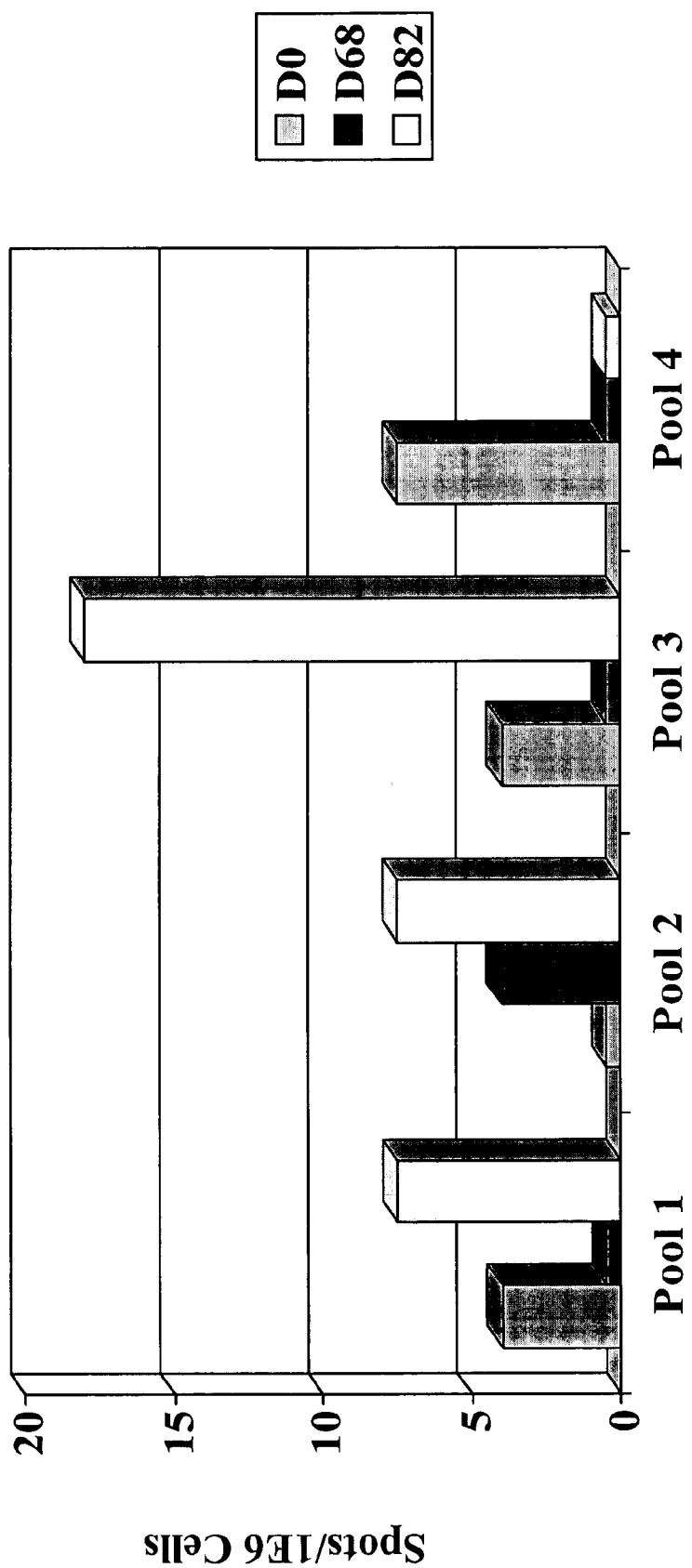
FIG. 4 is a bar graph showing the results of an IFN-γ-ELISPOT analysis of an animal receiving a subcutaneous injection of the tumor antigen.

As hereinbefore mentioned, the present invention relates to an improved method for inducing and/or enhancing the immune response to a tumor antigen. Accordingly, the present invention provides a method for inducing and/or enhancing an immune response in an animal to a tumor antigen comprising administering an effective amount of a tumor antigen, a nucleic acid sequence encoding a tumor antigen, a vector or cell comprising the nucleic acid sequence, or a vaccine comprising the tumor antigen, the nucleic acid sequence encoding the tumor antigen, or a vector comprising the nucleic acid sequence encoding the tumor antigen to a lymphatic site in the animal.

The term "inducing and/or enhancing an immune response" means that the method evokes and/or enhances any response of the animal's immune system.

"Immune response" is defined as any response of the immune system, for example, of either a cell-mediated (i.e. cytotoxic T-lymphocyte mediated) or humoral (i.e. antibody mediated) nature. These immune responses can be assessed by a number of in vivo or in vitro assays well known to one skilled in the art including, but not limited to, antibody assays (for example ELISA assays) antigen specific cytotoxicity assays, production of cytokines (for example ELISPOT assays), regression of tumors expressing the tumor antigens, inhibition of cancer cells expressing the tumor antigens, etc.

The term "lymphatic site" means a site in the body that is associated with the lymphatic system including lymphatic organs, tissues, cells, nodes or glands such as spleen, thymus, tonsils, Peyers patches, bone marrow, lymphocytes, thoracic duct as well as all of the lymph nodes of the body.

The term "animal" as used herein includes all members of the animal kingdom and is preferably human.

The term "effective amount" as used herein means an amount effective, at dosages and for periods of time necessary to achieve the desired results.

The term "tumor antigen" as used herein includes both tumor associated antigens (TAAs) and tumor specific antigens (TSAs). A tumor associated antigen means an antigen that is expressed on the surface of a tumor cell in higher amounts than is observed on normal cells or an antigen that is expressed on normal cells during fetal development. A tumor specific antigen is an antigen that is unique to tumor cells and is not expressed on normal cells. The term tumor antigen includes TAAs or TSAs that have been already identified and those that have yet to be identified and includes fragments, epitopes and any and all modifications to the tumor antigens.

The tumor associated antigen can be any tumor associated antigen including, but not limited to, gp100 (Kawakami et al., *J. Immunol.* 154:3961-3968 (1995): Cox et al., *Science*, 264: 716-719 (1994)), MART-1/Melan A (Kawakami et al., *J. Exp. Med.*, 180, 347-352 (1994); Castelli et al., *J. Exp. Med.*, 181:363-368 (1995)), gp75 (TRP-1) (Wang et al., *J. Exp. Med.*, 186:1131-1140 (1996)), and Tyrosinase (Wolfel et al., *Eur. J. Immunol.*, 24:759-764 (1994); Topalian et al., *J. Exp. Med.*, 183:1965-1971 (1996)); melanoma proteoglycan (Helistrom et al., *J. Immunol.*, 130:1467-1472 (1983): Ross et al., *Arch. Biochem Biophys.*, 225:370-383 (1983)); tumor-specific, widely shared antigens, for example: antigens of MAGE family, for example, MAGE-1, 2, 3, 4, 6, and 12 (Van der Bruggen et al., *Science*, 254:1643-1647 (1991); Rogner et al., *Genomics*, 29:729-731 (1995)), antigens of BAGE family (Boel et al., *Immunity*, 2:167-175 (1995)), antigens of GAGE family, for example, GAGE-1,2 (Van den Eynde et al., *J. Exp. Med.*, 182:689-698 (1995)), antigens of RAGE family, for example, RAGE-1 (Gaugler et al., *Immunogenetics*, 44:323-330 (1996)). N-acetylglucosaminyltransferase-V (Guilloux et al., *J. Exp. Med.*, 183:1173-1183 (1996)), and p15 (Robbins et al., *J. Immunol.* 154:5944-5950 (1995)); tumor specific mutated antigens; mutated β-catenin (Robbins et al., *J. Exp. Med.*, 183:1185-1192 (1996)), mutated MUM-1 (Gaulle et al., *Proc. Natl. Acad. Sci. USA*, 92:7976-7980 (1995)), and mutated cyclin dependent kinases-4 (CDK4) (Wolfel et al., *Science*, 269:1281-1284 (1995)); mutated oncogene products: p21 ras (Fossum et al., *Int. J. Cancer*, 56:40-45 (1994)), BCR-abl (Bocchia et al., *Blood*, 85:2680-2684 (1995)), p53 (Theobald et al., *Proc. Natl. Acad. Sci. USA*, 92:11993-11997 (1995)), and p185 HER2/neu (Fisk et al., *J. Exp. Med.*, 181-2109-2117 (1995)); Peoples et al., *Proc Natl. Acad. Sci., USA*, 92.432-436 (1995)); mutated epidermal growth factor receptor (EGFR) (Fujimoto et al., *Eur. J. Gynecol. Oncol.*, 16:40-47 (1995)); Harris et al., Breast Cancer Res. Treat, 29:1-2 (1994)); carcinoembryonic antigens (CEA) (Kwong et al., *J. Natl Cancer Inst.*, 85:982-990 (1995)); carcinoma associated mutated mucins, for example, MUC-1 gene products (Jerome et al., *J Immunol.*, 151:1654-1662 (1993), Ioannides et al., *J. Immunol.*, 151:3693-3703 (1993), Takahashi at al., *J. Immunol.*, 153:2102-2109 (1994)); EBNA gene products of EBV, for example, EBNA-1 gene product (Rickinson et al., *Cancer Surveys*, 13:53-80 (1992)); E7, E6 proteins of human papillomavirus (Ressing et al., *J. Immunol*, 154:5934-5943 (1995)); prostate specific antigens (PSA) (Xue et al., *The Prostate*, 30:73-78 (1997)); prostate specific membrane antigen (PSMA) (Israeli, at al., *Cancer Res.*, 54:1807-1811 (1994)); PCTA-1 (Sue et al., *Proc. Natl. Acad. Sci. USA*, 93:7252-7257 (1996)); idiotypic epitopes or antigens, for example, immunoglobulin idiotypes or T cell receptor idiotypes, (Chen et al., *J. Immunol.*, 153:4775-4787 (1994); Syrengelas at al, *Nat. Med.*, 2:1038-1040 (1996)); KSA (U.S. Pat. No. 5,348,887); NY-ESO-1 (WO 98/14464).

Also included are modified tumor antigens and/or epitope/peptides derived therefrom (both unmodified and modified). Examples include, but are not limited to, modified and unmodified epitope/peptides derived from gp100 (WO 98/02598; WO 95/29193; WO 97/34613; WO 98/33810; CEA (WO 99/19478; S. Zaremba at al. (1997) *Cancer Research* 57:4570-7; KT. Tsang at al. (1995) *J. Int. Cancer Inst.* 87:982-90); MART-1 (WO 98/58951, WO 98/02538; D. Valmen at al. (2000) *J. Immunol.* 164:1125-31); p53 (M. Eura et al. (2000) *Clinical Cancer Research* 6.979-86); TRP-1 and TRP-2 (WO 97/29195); tyrosinase (WO 96/21734; WO 97/11669; WO 97/34613; WO 98/33810; WO 95/23234; WO 97/26535); KSA (WO 97/15597); PSA (WO 96/40754); NY-ESO 1 (WO 99/18206); HER2/neu (U.S. Pat. No. 5,869,445); MAGE family related (L. Heidecker et al. (2000) *J. Immunol.* 164:6041-5; WO 95/04542; WO 95/25530; WO 95/25739; WO 96/26214; WO 97/31017; WO 98/10780).

In a preferred embodiment, the tumor-associated antigen is gp100, a modified gp100 or a fragment thereof. In particular, the inventors have prepared a modified gp100 peptide termed gp100M which has the nucleic acid sequence shown in FIG. 6 (SEQ.ID.NO.:109) and the deduced amino acid sequence shown in FIG. 7 (SEQ.ID.NO.:110). The inventors have shown that the intranodal injection of a recombinant avipox virus comprising a nucleic acid coding for fragments of the modified gp100 (comprising modified epitopes 209(2M) (IMDQVPFSY, SEQ.ID.NO.:1) and 290(9V) (YLEPGPVIV, SEQ.ID.NO.:2)) followed by modified epitope/peptide boosts induced both a humoral and cell mediated response that was several times higher than when the same antigens were administered subcutaneously. The experimental details and results are discussed in Example 1.

In another embodiment, the tumor-associated antigen is carcinoembryonic antigen (CEA), a modified CEA or a fragment thereof. The nucleic acid sequence of a modified CEA antigen is shown in FIG. 8 and SEQ.ID.NO.:111. The corresponding amino acid sequence is shown in FIG. 8 and SEQ.ID.NO.:112. Preferably, the modified CEA antigen comprises the sequence YLSGADLNL, SEQ.ID.NO.:113.

Additional embodiments of the invention encompass nucleic acid sequences comprising sequences encoding the tumor antigens and fragments or modified forms thereof as hereinbefore described. The term "nucleic acid sequence" refers to a sequence of nucleotide or nucleoside monomers consisting of naturally occurring bases, sugars and intersugar (backbone) linkages. The term also includes modified or substituted sequences comprising non-naturally occurring monomers or portions thereof, which function similarly. The nucleic acid sequences of the present invention may be ribonucleic (RNA) or deoxyribonucleic acids (DNA) and may contain naturally occurring bases including adenine, guanine, cytosine, thymidine and uracil The sequences may also contain modified bases such as xanthine, hypoxanthine, 2-aminoadenine, 6-methyl, 2-propyl, and other alkyl adenines, 5-halo uracil, 5-halo cytosine, 6-aza uracil, 6-aza cytosine and 6-aza thymine, pseudo uracil, 4-thiouracil, 8-halo adenine, 8-amino adenine, 8-thiol adenine, 8-thio-alkyl adenines. 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

The nucleic acid sequences encoding the tumor antigens of the invention include, but are not limited to, viral nucleic acid(s), plasmid(s), bacterial DNA, naked/free DNA and RNA. The nucleic acids encompass both single and double stranded forms. As such, these nucleic acids comprise the relevant base sequences coding for the aforementioned tumor antigens. For purposes of definitiveness, the "relevant base sequences coding for the aforementioned polypeptides" further encompass complementary nucleic acid sequences. As such, embodiments of the invention encompass nucleic acid sequences per se encoding for the aforementioned tumor antigens, or recombinant nucleic acids into which has been inserted said nucleic acids coding for tumor antigens (as described below).

Bacterial DNA useful in recombinant nucleic acid embodiments of the invention are Known to those of ordinary skill in the art. Sources of bacterial DNA include, for example, *Shigella*, *Salmonella*, *Vibrio cholerae*, *Lactobacillus*, Bacille Calmette Guérin (BCG), and *Streptococcus*. In bacterial DNA embodiments of the invention, nucleic acid of the invention may be inserted into the bacterial genome, can remain in a free state, or be carried on a plasmid.

Viral recombinant nucleic acid embodiments of the invention may be derived from a poxvirus or other virus such as adenovirus or alphavirus. Preferably the viral nucleic acid is incapable of integration in recipient animal cells. The elements for expression from said nucleic acid may include a promoter suitable for expression in recipient animal cells.

Specific vial recombinant nucleic acid embodiments of the invention encompass (but are not limited to) poxyiral, alphaviral, and adenoviral nucleic acid. Poxyiral nucleic acid may be selected from the group consisting of avipox, orthopox, and suipox nucleic acid. Particular embodiments encompass poxyiral nucleic acid selected from vaccinia, fowlpox, canary pox and swinepox; specific examples include TROVAC, NYVAC, ALVAC, MVA, Wyeth and Poxyac-TC (described in more detail below).

It is further contemplated that recombinant nucleic acids of this invention may further comprise nucleic acid sequences encoding at least one member chosen from the group consisting of cytokines, lymphokines, and co-stimulatory molecules. Examples include (but are not limited to) interleukin 2, interleukin 12, interleukin 6, interferon gamma, tumor necrosis factor Alpha, GM-CSF, B7.1, B7.2, ICAM-1, LFA-3, and Cd72.

Standard techniques of molecular biology for preparing and purifying nucleic acids well known to those skilled in the art can be used in the preparation of the recombinant nucleic acid aspects of the invention (for example, as taught in *Current Protocols in Molecular Biology*, F. M. Ausubel et al. (Eds.), John Wiley and Sons, Inc, N.Y., U.S.A. (1998), Chpts. 1, 2 and 4; *Molecular Cloning: A Laboratory Manual* (2$^{nd}$ Ed.), J. Sambrook, E. F. Fritsch and T. Maniatis (Eds.), Cold Spring Harbor Laboratory Press, N.Y., U.S.A. (1989), Chpts. 1, 2, 3 and 7).

Aspects of this invention further encompass vectors comprising the aforementioned nucleic acids. In certain embodiments, said vectors may be recombinant viruses or bacteria (as described below)

Adenovirus vectors and methods for their construction have been described (e.g. U.S. Pat. Nos. 5,994,132, 5,932, 210, 6,057,158 and Published PCT Applications WO 9817783, WO 9744475, WO 9961034, WO 9950292, WO 9927101, WO 9720575, WO 9640955, WO 9630534-all of which are herein incorporated by reference). Alphavirus vectors have also been described in the art and can be used in embodiments of this invention (e.g. U.S. Pat. Nos. 5,792,462, 5,739,026, 5,843,723, 5,789,245, and Published PCT Applications WO 9210578, WO 9527044, WO 9531565, WO 9815636-all of which are herein incorporated by reference), as have lentivirus vectors (e.g. U.S. Pat. Nos. 6,013,516, 5,994,136 and Published PCT Applications WO 9817816, WO 9712622. WO 9817815, WO 9839463, WO 9846083, WO 9915641, WO 9919501, WO 9930742, WO 9931251, WO 9851810, WO 0000600-all of which are herein incorporated by reference). Poxvirus vectors that can be used include, for example, avipox, *orthopox* or suipox poxvirus (as described in U.S. Pat. Nos. 5,364,773, 4,603,112, 5,762,938, 5,378,457, 5,494,807, 5,505,941, 5,756,103, 5,833,975 and 5,990,091-all of which are herein incorporated by reference). Poxvirus vectors comprising a nucleic acid coding for a tumor antigen can be obtained by homologous recombination as is known to one skilled in the art. As such, the nucleic acid coding for the tumor antigen is inserted into the viral genome under appropriate conditions for expression in mammalian cells (as described below).

In one embodiment of the invention the poxvirus vector is ALVAC (1) or ALVAC (2) (both of which have been derived from canarypox virus). ALVAC (1) (or ALVAC (2)) does not productively replicate in non-avian hosts, a characteristic thought to improve its safety profile. ALVAC (1) is an attenuated canarypox virus-based vector that was a plaque-cloned derivative of the licensed canarypox vaccine, Kanapox (Tartaglia et al. (1992) *Virology* 188:217; U.S. Pat. Nos. 5,505,941, 5,756,103 and 5833975-all of which are incorporated herein by reference). ALVAC (1) has some general properties which are the same as some general properties of Kanapox. ALVAC-based recombinant viruses expressing extrinsic immunogens have also been demonstrated efficacious as vaccine vectors (Tartaglia et al, In AIDS Research Reviews (vol. 3) Koff W., Wong-Staol F. and Kenedy R. C. (eds.), Marcel Dekker NY, pp. 361-378 (1993a). Tartaglia, J. et al. (1993b) *J. Virol.* 67:2370). For instance, mice immunized with an ALVAC (1) recombinant expressing the rabies virus glycoprotein were protected from lethal challenge with rabies virus (Tartaglia, J et al., (1992) supra) demonstrating the potential for ALVAC (1) as a vaccine vector. ALVAC-based recombinants have also proven efficacious in dogs challenged with canine distemper virus (Taylor, J. et al (1992) Virology 187:321) and rabies virus (Perkus, M. E. et al., In Combined Vaccines and Simultaneous Administration: Current Issues and Perspective, Annals of the New York Academy of Sciences (1994)), in cats challenged with feline leukemia virus (Tartaglia, J. et al., (1993b) supra), and in horses challenged with equine influenza virus (Taylor, J. et al., In Proceedings of the Third International Symposium on Avian Influenza, Univ. of Wisconsin-Madison, Madison, Wis., pp. 331-335 (1993)).

ALVAC (2) is a second-generation ALVAC vector in which vaccinia transcription elements E3L and K3L have been inserted within the C6 locus (U.S. Pat. No. 5,990,091, incorporated herein by reference). The E3L encodes a protein capable of specifically binding to dsRNA. The K3L ORF has significant homology to E1F-2. Within ALVAC (2) the E3L gene is under the transcriptional control of its natural promoter, whereas K3L has been placed under the control of the early/late vaccine H6 promoter. The E3L and K3L genes act to inhibit PKR activity in cells infected with ALVAC allowing enhancement of the level and persistence of foreign gene expression.

Additional viral vectors encompass natural host-restricted poxviruses. Fowlpox virus (FPV) is the prototypic virus of the Avipox genus of the Poxvirus family. Replication of avipox viruses is limited to avian species (Matthews, R. E. F. (1982) *Intervirology* 17:42) and there are no reports in the literature of avipox virus causing a productive infection in any non-avian species including man. This host restriction provides an inherent safety barrier to transmission of the virus to other species and makes use of avipox virus based vectors in veterinary and human applications an attractive proposition.

FPV has been used advantageously as a vector expressing immunogens from poultry pathogens. The hemagglutinin protein of a virulent avian influenza virus was expressed in an FPV recombinant. After inoculation of the recombinant into chickens and turkeys, an immune response was induced which was protective against either a homologous or a heterologous virulent influenza virus challenge (Taylor, J. et al (1988) *Vaccine* 6: 504) FPV recombinants expressing the surface glycoproteins of Newcastle Disease Virus have also been developed (Taylor, J. et al. (1990) *J. Vitol.* 64:1441; Edbauer, C. et al. (1990) *Virology* 179:901; U.S. Pat. No. 5,766,599-incorporated herein by reference).

A highly attenuated strain of vaccinia, designated MVA, has also been used as a vector for poxvirus-based vaccines. Use of MVA is described in U.S. Pat. No. 5,185,146.

Other attenuated poxvirus vectors have been prepared via genetic modification to wild type strains of vaccinia. The NYVAC vector, for example, is derived by deletion of specific virulence and host-range genes from the Copenhagen strain of vaccinia (Tartaglia, J. et al. (1992), supra; U.S. Pat. Nos. 5,364,773 and 5,494,807-incorporated herein by reference) and has proven useful as a recombinant vector in eliciting a protective immune response against expressed foreign antigens.

Recombinant viruses can be constructed by processes known to those skilled in the art (for example, as previously described for vaccinia and avipox viruses; U.S. Pat. Nos. 4,769,330; 4,722,848; 4,603,112; 5,110,587; and 5,174,993-all of which are incorporated herein by reference).

In further embodiments of the invention, live and/or attenuated bacteria may also be used as vectors. For example, non-toxicogenic *Vibrio cholerae* mutant strains may be useful as bacterial vectors in embodiments of this invention; as described in U.S. Pat. No. 4,882,278 (disclosing a strain in which a substantial amount of the coding sequence of each of the two ctxA alleles has been deleted so that no functional cholera toxin is produced), WO 92/11354 (strain in which the irgA locus is inactivated by mutation, this mutation can be combined in a single strain with ctxA mutations), and WO 94/1533 (deletion mutant lacking functional ctxA and attRS1 DNA sequences). These strains can be genetically engineered to express heterologous antigens, as described in WO 94/19482. (All of the aforementioned issued patent/patent applications are incorporated herein by reference.)

Attenuated *Salmonella typhimurium* strains, genetically engineered for recombinant expression of heterologous antigens and their use as oral immunogens are described, for example, in WO 92/11361.

As noted, those skilled in the art will readily recognize that other bacterial strains useful as bacterial vectors in embodiments of this invention include (but are not limited to) *Shigella flexneri, Streptococcus gordonii*, and Bacille Calmette Guerin (as described in WO 88/6626, WO 90/0594, WO 91/13157, WO 92/1796, and WO 92/21376; all of which are incorporated herein by reference). In bacterial vector embodiments of this invention, a nucleic acid coding for a tumor antigen may be inserted into the bacterial genome, can remain in a free state, or be carried on a plasmid.

It is further contemplated that the invention encompasses vectors which comprise nucleic acids coding for at least one member from the group consisting of cytokines, lymphokines and immunostimulatory molecules. Said nucleic acid sequences can be contiguous with sequences coding for the tumor antigen or encoded on distinct nucleic acids.

Cells comprising the aforementioned tumor antigens, nucleic acids coding therefor, and/or vectors encompass further embodiments of the invention These cells encompass any potential cell into which the aforementioned tumor antigen, nucleic acid, and/or vector might be introduced and/or transfected and/or infected (for example, bacteria, COS cells, Vero cells, chick embryo fibroblasts, tumor cells, antigen presenting cells, dendritic cells, etc.). The choice of process for the introduction and/or transfection and/or infection into cells is dependant upon the intrinsic nature of the introduced agent (i.e. free DNA, plasmid, recombinant virus), as will be known to one skilled in the art (for example, as taught in *Current Protocols in Molecular Biology*, F. M. Ausubel et al. (Eds.), John Wiley and Sons, Inc., N.Y., U.S.A. (1998), Chpt. 9; *Molecular Cloning: A Laboratory Manual* (2nd Ed), J. Sambrook, E. F. Fritsch and T Maniatis (Eds.), Cold Spring Harbor Laboratory Press, N.Y., U.S.A. (1989), Chpts. 1, 2, 3 and 16).

Further embodiments of the invention encompass vaccines comprising the tumor antigens and/or nucleic acids coding therefor and/or vectors and/or cells previously described.

The vaccine of the invention comprising the tumor antigen may be a multivalent vaccine and additionally contain several peptides, epitopes or fragments of a particular tumor antigen or contain peptides related to other tumor antigens and/or infectious agents in a prophylactically or therapeutically effective manner. Multivalent vaccines against cancers may contain a number of individual TAA's, or immunogenic fragments thereof, alone or in combinations which are effective to modulate an immune response to cancer.

A vaccine of the invention may contain a nucleic acid molecule encoding a tumor antigen of the invention. Such vaccines are referred to as nucleic acid vaccines but are also termed genetic vaccines, polynucleotide vaccines or DNA vaccines, all of which are within the scope of the present invention. In such an embodiment, the tumor antigen is produced in vivo in the host animal. Additional embodiments if the invention encompass vectors (i.e. bacteria, recombinant viruses) comprising the aforementioned nucleic acids.

The present invention also contemplates mixtures of the tumor antigens, nucleic acids coding therefor, vectors comprising said nucleic acids, cells and/or vaccines comprising the aforementioned, and at least one member selected from the group consisting of cytokines, lymphokines, immunostimulatory molecules, and nucleic acids coding therefor. Additional embodiments of this invention further encompass pharmaceutical compositions comprising the aforementioned tumor antigens, nucleic acids coding therefor, vectors, cells, vaccines or mixtures for administration to subjects in a biologically compatible form suitable for administration in vivo. By "biologically compatible form suitable for administration in vivo" is meant a form of the substance to be administered in which any toxic effects are outweighed by the therapeutic effects. Administration of a therapeutically active amount of the pharmaceutical compositions of the present invention, or an "effective amount", is defined as an amount effective at dosages and for periods of time, necessary to achieve the desired result of eliciting an immune response in an animal. A therapeutically effective amount of a substance may vary according to factors such as the disease state/health, age, sex, and weight of the recipient, and the inherent ability of the particular tumor antigen, nucleic acid coding therefor, vector, cell, or vaccine to elicit a desired immune response. Dosage regime may be adjusted to provide the optimum therapeutic response. For example, several divided doses may be administered daily, or at periodic intervals, and/or the dose may be proportionally reduced as indicated by the exigencies of circumstances.

The pharmaceutical compositions described herein can be prepared by per se known methods for the preparation of pharmaceutically acceptable compositions which can be administered to animals such that an effective quantity of the active substance (i.e. tumor antigen, nucleic acid, recombinant virus, vaccine) is combined in a mixture with a pharmaceutically acceptable vehicle. Suitable vehicles are described, for example, in "Handbook of Pharmaceutical Additives" (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456. These compositions may further comprise an adjuvant (as described below).

Further embodiments of the invention encompass methods of inhibiting a tumor antigen expressing cancer cell in a patient comprising administering to said patient an effective amount of a tumor antigen, nucleic acid coding therefor, vector, cell, or vaccine of the invention. Patients with solid tumors expressing tumor antigens include (but are not limited to) those suffering from colon cancer, lung cancer, pancreas cancer, endometrial cancer, breast cancer, thyroid cancer, melanoma, oral cancer, laryngeal cancer, seminoma, hepatocellular cancer, bile duct cancer, squamous cell carcinoma, and prostate cancer. As such, methods of treating patients with cancer per se encompassing the aforementioned methods of inducing an immune response and/or inhibiting a tumor antigen expressing cell are contemplated aspects/embodiments of the invention.

As mentioned previously, an animal may be immunized with a tumor antigen, nucleic acid coding therefore, vector, cell or vaccine of the invention by administering the aforementioned to a lymphatic site. The administration can be achieved in a single dose or repeated at intervals. The appropriate dosage is dependant on various parameters understood by the skilled artisans, such as the immunogen itself (i.e. polypeptide vs. nucleic acid (and more specifically type thereof)), the route of administration and the condition of the animal to be vaccinated (weight, age and the like).

As previously noted, nucleic acids (in particular plasmids and/or free/naked DNA and/or RNA coding for the tumor antigen of the invention) can be administered to an animal for purposes of inducing/eliciting an immune response (for example, U.S. Pat. No. 5,589,466; McDonnell and Askari, *NEJM* 334:42-45 (1996); Kowalczyk and Ertl, *Cell Mol. Life. Sci.* 55:751-770 (1999)). Typically, this nucleic acid is a form that is unable to replicate in the target animal's cell and unable to integrate in said animal's genome. The DNA/RNA molecule encoding the tumor antigen is also typically placed under the control of a promoter suitable for expression in the animal's cell. The promoter can function ubiquitously or tissue-specifically Examples of non-tissue specific promoters include the early Cytomegalovirus (CMV) promoter (described in U.S. Pat. No. 4,168,062) and the Rous Sarcoma Virus promoter. The desmin promoter is tissue-specific and drives expression in muscle cells. More generally, useful vectors have been described (i.e., WO 94/21797).

For administration of nucleic acids coding for a tumor antigen, said nucleic acid can encode a precursor or mature form of the polypeptide/protein. When it encodes a precursor form, the precursor form can be homologous or heterologous. In the latter case, a eucaryotic leader sequence can be used, such as the leader sequence of the tissue-type plasminogen factor (tPA).

For use as an immunogen, a nucleic acid of the invention can be formulated according to various methods known to a skilled artisan. First, a nucleic acid can be used in a naked/free form, free of any delivery vehicles (such as anionic liposomes, cationic lipids, microparticles, (e.g., gold microparticles), precipitating agents (e.g., calcium phosphate) or any other transfection-facilitating agent. In this case the nucleic acid can be simply diluted in a physiologically acceptable solution (such as sterile saline or sterile buffered saline) with or without a carrier. When present, the carrier preferably is isotonic, hypotonic, or weakly hypertonic, and has a relatively low ionic strength (such as provided by a sucrose solution (e.g., a solution containing 20% sucrose)).

Alternatively, a nucleic acid can be associated with agents that assist in cellular uptake. It can be, i.e. (i) complemented with a chemical agent that modifies the cellular permeability (such as bupivacaine; see, for example, WO 94/16737), (ii) encapsulated into liposomes, or (iii) associated with cationic lipids or silica, gold, or tungsten microparticles.

Cationic lipids are well known in the art and are commonly used for gene delivery. Such lipids include Lipofectin (also known as DOTMA (N-[1-(2,3-dioleyloxy)propyl]-N,N,N-trimethylammonium chloride), DOTAP (1,2-bis(oleyloxy)-3-(trimethylammonio) propane). DDAB (dimethyldioctadecyl-ammonium bromide), DOGS (dioctadecylamidologlycyl spermine) and cholesterol derivatives such as DC-Chol (3 beta-(N—(N',N'-dimethyl aminomethane)-carbamoyl) cholesterol). A description of these cationic lipids can be found in EP 187702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine) as, for example, described in WO 90/11092.

Other transfection-facilitating compounds can be added to a formulation containing cationic liposomes. A number of them are described in, for example, WO 93/18759, WO 93/19768, WO 94/25608, and WO 95/2397. They include, for example, spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles can also be used for nucleic acid delivery (as described in WO 91/359 and WO 93/17706). In this case, the microparticle-coated polynucleotides can be injected via intradermal or intraepidermal routes using a needleless injection device ("gene gun"; such is as those described, for example, in U.S. Pat. No. 4,945,050, U.S. Pat. No. 5,015,580, and WO 94/24263).

Anionic and neutral liposomes are also well-known in the art (see, for example, Liposomes: A Practical Approach, RPC New Ed, IRL Press (1990), for a detailed description of methods for making liposomes) and are useful for delivering a large range of products, including nucleic acids.

Particular embodiments of the aforementioned methods (i.e. to induce/elicit immune responses) encompass prime-boost protocols for the administration of immunogens of the invention. More specifically, these protocols encompass (but are not limited to) a "priming" step with a particular/distinct form of immunogen (i.e. nucleic acid (for example, plasmid, bacterial/viral/free or naked)) coding for tumor antigen, or vector (i.e. recombinant virus, bacteria) comprising said nucleic acid) followed by at least one "boosting" step encompassing the administration of an alternate (i.e. distinct from that used to "prime") form of the tumor antigen (i.e. protein or fragment thereof (for example, epitope/peptide), nucleic acid coding for the tumor antigen (or fragment thereof), or vector comprising said nucleic acid). Examples of "prime-boost" methodologies are known to those skilled in the art (as taught, for example, in PCT published applications WO 98/58956, WO 98/56919, WO 97/39771). One advantage of said protocols is the potential to circumvent the problem of generating neutralizing immune responses to vectors per se (i.e. recombinant viruses) wherein is inserted/incorporated nucleic acids encoding the immunogen or fragments thereof (see for example, R. M. Conry et al (2000) *Clin. Cancer Res.* 6.34-41).

As is well known to those of ordinary skill in the art, the ability of an immunogen to induce/elicit an immune response can be improved if, regardless of administration formulation (i.e. recombinant virus, nucleic acid, polypeptide), said immunogen is co-administered with an adjuvant. Adjuvants are described and discussed in "Vaccine Design—the Subunit and Adjuvant Approach" (edited by Powell and Newman, Plenum Press, New York, U.S.A., pp. 61-79 and 141-228 (1995)). Adjuvants typically enhance the immunogenicity of an immunogen but are not necessarily immunogenic in and of themselves. Adjuvants may act by retaining the immunogen locally near the site of administration to produce a depot effect facilitating a slow, sustained release of immunizing agent to cells of the immune system. Adjuvants can also attract cells of the immune system to an immunogen depot and stimulate such cells to elicit immune responses. As such, embodiments of this invention encompass compositions further comprising adjuvants.

Desirable characteristics of ideal adjuvants include:
1) lack of toxicity;
2) ability to stimulate a long-lasting immune response;
3) simplicity of manufacture and stability in long-term storage;
4) ability to elicit bath cellular and humoral responses to antigens administered by various routes, if required;
5) synergy with other adjuvants:
6) capability of selectively interacting with populations of antigen presenting cells (APC);
7) ability to specifically elicit appropriate TH1 or TH2 cell-specific immune responses: and
8) ability to selectively increase appropriate antibody isotype levels (for example, IgA) against antigens/immunogens.

However, many adjuvants are toxic and can cause undesirable side effects, thus making them unsuitable for use in humans and many animals. For example, some adjuvants may induce granulomas, acute and chronic inflammations (i.e Freund's complete adjuvant (FCA)), cytolysis (i.e. saponins and pluronic polymers) and pyrogenicity, arthritis and anterior uveitis (i.e. muramyl dipeptide (MDF) and lipopolysaccharide (LPS)). Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established. Notwithstanding, it does have limitations. For example, alum is ineffective for influenza vaccination and inconsistently elicits a cell mediated immune response with other immunogens. The antibodies elicited by alum-adjuvanted antigens are mainly of the IgG1 isotype in the mouse, which may not be optimal for protection in vaccination contexts.

Adjuvants may be characterized as "intrinsic" or "extrinsic". Intrinsic adjuvants (such as lipopolysaccharides) are integral and normal components of agents which in themselves are used as vaccines (i.e. killed or attenuated bacteria). Extrinsic adjuvants are typically nonintegral immunomodulators generally linked to antigens in a noncovalent manner, and are formulated to enhance the host immune response In embodiments of the invention, adjuvants can be at least one member chosen from the group consisting of cytokines, lymphokines, and co-stimulatory molecules. Examples include (but are not limited to) interleukin 2, interleukin 12, interleukin 6, interferon gamma, tumor necrosis factor alpha, GM-CSF, B7.1, B7.2, ICAM-1, LFA-3, and CD72. Particular embodiments specifically encompass the use of GM-CSF as an adjuvant (as taught, for example, in U.S. Pat. Nos. 5,679,356, 5,904,920, 5,637,483, 5,759,535, 5,254,534, European Patent Application EP 211684, and published PCT document WO 97/28816—all of which are herein incorporated by reference).

A variety of potent extrinsic adjuvants have been described. These include (but are not limited to) saponins complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

The use of saponins per se as adjuvants is also well Known is (Lacaille-Dubois, M. and Wagner, H. (1996) *Phytomedicine* 2:363). For example, Quit A (derived from the bark of the South American tree Quillaja Saponaria Molina) and fractions thereof has been extensively described (i.e. U.S. Pat. No. 5,057,540; Kensil, C. R. (1996) *Crit Rev Ther Drug Carrier Syst.* 12:1; and European Patent EP 362279). The haemolytic saponins QS21 and QS17 (HPLC purified fractions of Quil A) have been described as potent systemic adjuvants (U.S. Pat. No. 5,057,540; European Patent EP 362279). Also described in these references is the use of QS7 (a non-haemolytic fraction of Quil-A) which acts as a potent adjuvant for systemic vaccines. Use of QS21 is further described in Kensil et al. ((1991) *J. Immunol* 146:431). Combinations of QS21 and polysorbate or cyclodextrin are also known (WO 9910008). Particulate adjuvant systems comprising fractions of Quil A (such as QS21 and QS7) are described in WO 9633739 and WO 9611711

Another preferred adjuvant/immunostimulant is an immunostimulatory oligonucleotide containing unmethylated CpG dinucleotides ("CpG"). CpG is an abbreviation for cytosine-guanosine dinucleotide motifs present in DNA. CpG is known in the art as being an adjuvant when administered by both systemic and mucosal routes (WO 9602555: European Patent EP 468520; Davies et al (1998) *J. Immunol.* 160:87; McCluskie and Davis (1998) *J. Immunol.* 161:4463) In a number of studies, synthetic oligonucleotides derived from BCG gene sequences have also been shown to be capable of inducing immunostimulatory effects (both in vitro and in vivo; Krieg, (1995) *Nature* 374:546). Detailed analyses of immunostimulatory oligonucleotide sequences has demonstrated that the CG motif must be in a certain sequence context, and that such sequences are common in bacterial DNA but are rare in vertebrate DNA. (For example, the immunostimulatory sequence is often: purine, purine, C, G, pyrimidine, pyrimidine, wherein the CG motif is not methylated; however other unmethylated CpG sequences are known to be immunostimulatory and as such may also be used in the present invention.) As will be evident to one of normal skill in the art, said CG motifs/sequences can be incorporated into nucleic acids of the invention per se, or reside on distinct nucleic acids.

A variety of other adjuvants are taught in the art, and as such are encompassed by embodiments of this invention. U.S. Pat. No. 4,855,283 granted to Lockhoff et al. (incorporated herein by reference) teaches glycolipid analogues and their use as adjuvants. These include N-glycosylamides, N-glycosylureas and N-glycosylcarbamates, each of which is substituted in the sugar residue by an amino acid, as immunomodulators or adjuvants. Furthermore, Lockhoff et al. ((1991) *Chem. Int. Ed. Engl.* 30:1611) have reported that N-glycolipid analogs displaying structural similarities to the naturally-occurring glycolipids (such as glycophospholipids and glycoglycerolipids) are also capable of eliciting strong immune responses in both herpes simplex virus vaccine and pseudorabies virus vaccine.

U.S. Pat. No. 4,258,029 granted to Moloney (incorporated herein by reference) teaches that octadecyl tyrosine hydrochloride (OTH) functions as an adjuvant when complexed with tetanus toxoid and formalin inactivated type I, II and III poliomyelitis virus vaccine. Nixon-George et al. ((1990) *J. Immunol.* 14:4798) have also reported that octadecyl esters of aromatic amino acids complexed with a recombinant hepatitis B surface antigen enhanced the host immune responses against hepatitis B virus.

Adjuvant compounds may also be chosen from the polymers of acrylic or methacrylic acid and the copolymers of maleic anhydride and alkenyl derivative. Adjuvant compounds are the polymers of acrylic or methacrylic acid which are cross-linked, especially with polyalkenyl ethers of sugars or polyalcohols. These compounds are known by the term carbomer (Pharmeuropa Vol. 8, No. 2, June 1996). Preferably, a solution of adjuvant according to the invention, especially of carbomer, is prepared in distilled water, preferably in the presence of sodium chloride, the solution obtained being at acidic pH. This stock solution is diluted by adding it to the desired quantity (for obtaining the desired final concentration), or a substantial part thereof, of water charged with NaCl, preferably physiological saline (NaCL 9 g/l) all at once in several portions with concomitant or subsequent neutralization (pH 7.3 to 7.4), preferably with NaOH. This solution at physiological pH will be used as it is for mixing with the immunizing agent; said mixture being amenable to storage in the freeze-dried, liquid or frozen form.

Persons skilled in the art can also refer to U.S. Pat. No. 2,909,462 (incorporated herein by reference) which describes adjuvants encompassing acrylic polymers cross-linked with a polyhydroxylated compound having at least 3 hydroxyl groups (preferably not more than 8), the hydrogen atoms of the at least three hydroxyls being replaced by unsaturated aliphatic radicals having at least 2 carbon atoms. The preferred radicals are those containing from 2 to 4 carbon atoms (e.g. vinyls, allyls and other ethylenically unsaturated groups). The unsaturated radicals may themselves contain other substituents, such as methyl The products sold under the name Carbopol (BF Goodrich, Ohio. USA) are particularly appropriate. They are cross-linked with allyl sucrose or with allyl pentaerythritol. Among them, there may be mentioned Carbopol (for example, 974P, 934P and 971P). Among the copolymers of maleic anhydride and alkenyl derivative, the copolymers EMA (Monsanto; which are copolymers of maleic anhydride and ethylene, linear or cross-linked, (for example cross-linked with divinyl ether)) are preferred. Reference may be made to J. Fields et al. ((1960) *Nature* 186: 778) for a further description of these chemicals (incorporated (herein by reference).

In further aspects of this invention, adjuvants useful for parenteral administration of immunizing agent include aluminum compounds (such as aluminum hydroxide, aluminum phosphate, and aluminum hydroxy phosphate; but might also be a salt of calcium, iron or zinc, or may be an insoluble suspension of acylated tyrosine, or acylated sugars, canonically or anionically derivatised polysaccharides, or polyphosphazenes). The antigen can be precipitated with, or adsorbed onto, the aluminum compound according to standard protocols well known to those skilled in the art.

Other adjuvants encompassed by embodiments of this invention include lipid A (in particular 3-de-O-acylated monophosphoryl lipid A (3D-MPL). 3D-MPL is a well known adjuvant manufactured by Ribi Immunochem. Montana. It is often supplied chemically as a mixture of 3-de-O-acylated monophosphoryl lipid A with 4, 5, or 6 acylated chains. It can be prepared by the methods taught in GB 2122204B. A preferred form of 30-MPL is in the form of a particulate formulation having a particle size less than 0.2 µm in diameter (European Patent EP 689454).

Adjuvants for mucosal immunization may include bacterial toxins (e.g., the cholera toxin (CT), the *E. coli* heat-labile toxin (LT), the *Clostridium difficile* toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. A mutant having reduced toxicity may be used. Mutants have been described (e.g., in WO 95/17211 (Arg-7-Lys CT mutant), WO 96/6627 (Arg-192-Gly LT mutant), and WO 95/34323 (Arg-9-Lys and Glu-129-Gly PT mutant)). Additional LT mutants include, for example Ser-63-Lys, Ala-69-Gly, Glu-110-Asp, and Glu-112-Asp mutants. Other adjuvants (such as a bacterial monophosphoryl lipid A (MPLA)) of various sources (e.g., *E. coli, Salmonella minnesota, Salmonella typhimurium,* or *Shigella flexneri*) can also be used in the mucosal administration of immunizing agents.

Adjuvants useful for both mucosal and parenteral immunization include polyphosphazene (for example, WO 95/2415), DC-chol (3 b-(N—(N',N'-dimethyl aminomethane)-carbamoyl) cholesterol (for example, U.S. Pat. No. 5,283,185 and WO 96/14831) and QS-21 (for example, WO 88/9336).

Adjuvants/immunostimulants as described herein may be formulated together with carriers, such as for example liposomes, oil in water emulsions, and/or metallic salts including aluminum salts (such as aluminum hydroxide). For example, 3D-MPL, may be formulated with aluminum hydroxide (as discussed in EP 689454) or oil in water emulsions (as discussed in WO 9517210); QS21 may be advantageously formulated with cholesterol containing liposomes (as discussed in WO 9633739), in oil water emulsions (as discussed in WO 9517210) or alum (as discussed in WO 9815287). When formulated into vaccines, immunostimulatory oligonucleotides (i.e. CpGs) are generally administered in free solution together with free antigen (as discussed in WO 9602555; McCluskie and Davis (1998) Supra), covalently conjugated to an antigen (as discussed in WO 9816247), or formulated with a carrier such as aluminum hydroxide or alum (as discussed in Davies et al. Supra; Brazolot-Millan et al (1998) *Proc. Natl. Acad. Sci.* 95:15553).

Combinations of adjuvants/immunostimulants are also within the scope of this invention. For example, a combination of a monophosphoryl lipid A and a saponin derivative (as described in WO 9400153, WO 9517210, WO 9633739, WO 9856414, WO 9912565, WO 9911214) can be used, or more particularly the combination of QS21 and 3D-MPL (as described in WO 9400153). A combination of an immunostimulatory oligonucleotide and a saponin (such as QS21), or a combination of monophosphoryl lipid A (preferably 3D-MPL) in combination with an aluminum salt also form a potent adjuvant for use in the present invention.

The following non-limiting example is illustrative of the present invention:

EXAMPLES

Example 1

This example compares the intranodal injection with subcutaneous injection of a representative tumor antigen (modified gp100).
Methods and Experimental Design
Test System
Cynomolgus monkeys (*Macaca fascicularis*) purpose bred animals. Supplier: Siconbrec "Simian Conservation Breeding & Research Center Inc.", Fema Building, 44 Gil Puyat Avenue Makati, Metro Manila, Philippines.
Number of animals in the study: 12 (6 males and 6 females).
Age at initiation of treatment. 26 to 38 months.
    Body weight range at initiation of treatment (day-1)
    males: 1.73 to 2.34 kg
    females: 1.71 to 2.65 kg.
Animal Husbandry
    Housing: one air-conditioned room;
    temperature: 19 to 25° C. (target range),
    relative humidity: >40%
    air changes: minimum 8 air changes per hour,
    lighting cycle: 12 hours light (artificial)/12 hours dark.
    Caging: animals were housed singly in stainless steel mesh cages (approximately 540×810×760 mm).
    Diet: expanded complete commercial primate diet (Mazuri diet, Special Diet Services Ltd., Witham, Essex, CM8, 3AD, Great Britain) analyzed for chemical and bacterial contaminants.
Quantity distributed 100 g diet/animal/day.
In addition, animals received fruit daily (apple or banana)
Animals were fasted for at least 16 hours before blood sampling for clinical laboratory investigations and before necropsy.
    Water: drinking water ad libitum (via bottles)
    Contaminants: no known contaminants were present in diet or water at levels which might have interfered with achieving the objective of the study.
Pre-Treatment Procedures
    Animal health procedure: all animals received a clinical examination for ill-health on arrival and a veterinary clinical examination during the acclimatization period.
    Acclimatization period: at least 3 weeks between animal arrival and start of treatment.
Experimental Design
    Allocation to treatment groups was performed during the acclimatization period using a random allocation procedure based on body weight classes.
    Animals were assigned to the treatment groups shown in Table 1. The dose levels administered were shown in Table 2.
Administration of the Test/Control Articles
Group 1 and 2 Animals
    Method of administration: injection in the left inguinal lymph node. Animals were lightly anaesthetized before each administration by an intramuscular injection of ketmine hydrochloride (Imalgene® 500—Merial, Lyon, France). The same lymph node was injected on each occasion (left side). Each injection was followed by a local disinfection with iodine (Vétédine®—Vetoquinol, Lure, France).
Group 3
    Route: subcutaneous.
    Method of administration: bolus injection using a sterile syringe and needle introduced subcutaneously. Four injection sites were used followed by a local disinfection with iodine (Vétédine®—Vétoquinol, Lure, France). Animals were also lightly anaesthetized before each administration by an intramuscular injection of ketamine hydrochloride (Imalgene® 500—Merial, Lyon, France) in order to be under the same conditions as groups 1 and 2 animals.

Four injection sites in the dorsal cervical/interscapular regions were used as shown in Table 3.

ELISPOT Analysis

An ELISPOT assay was used in order to assess the cell mediated immune response generated in the monkeys in the various treatment groups. In particular, an ELISPOT IFNγ assay was used in order to measure IFNγ production from T lymphocytes obtained from the monkeys in response to gp100 antigens.

Materials and Methods

Plates: MILLIPORE Multiscreen HA plate/MAHA S45.10 (96 wells).

Capture antibodies: MABTECH monoclonal anti-IFNγ antibodies/G-Z4 1 mg/mL.

Detection antibodies: MABTECH monoclonal anti-IFNγ antibodies/7-B6-1-biotin 1 mg/mL.

Enzyme: SIGMA, Extravidin-PA conjuate/E2636

Substrate: BIORAD, NBT/BCIP—Alkaline phosphatase conjugate substrate kit/ref: 170-64 32.

Coating

Place 100 μL per well of capture antibodies at 1 μg/mL diluted at 1/1000 in carbonate bicarbonate buffer 0.1M pH 9.6 into the multiwell plate. Incubate overnight at 4° C. Wash 4 times in 1×PBS.

Saturation

Place 200 μL per well of RPMI supplemented with 10% FCS, non essential amino acids, pyruvate, Hepes buffer and Peni-Strepto. Incubate 2 hours at 37° C.

Test

Cells from the immunized animals are tested against (a) medium alone: (b) pooled peptides at a concentration of 1 mg/mL; and (c) a non specific stimulus (PMA-Iono) The pooled peptides used in this Example to stimulate IFN-γ production were derived from gp100 and are illustrated in Tables 4 to 7. The final volume of each sample is 200 μL. Incubate 20 hours at 37° C.

Wash 4 times in 1×PBS and 0.05% Tween 20.

Detection

Place 100 μL per well of detection antibodies at 1 μg/mL diluted in 1/1000 1×PBS, 1% BSA and 0.05% Tween 20. Incubate 2 hours at room temperature. Wash 4 times in 1×PBS and 0.05% Tween 20.

Reaction

Place 100 μL per well of Extravidin-PA conjugate diluted 1/6000 in 1×PBS, 1% BSA and 0.05% Tween 20. Incubate 45 minutes at room temperature. Wash 4 times in 1×PBS and 0.05% Tween 20.

Substrate Addition

Place 100 μL per well of substrate previously prepared. For example, for 1 plate, prepare 9.6 mL of distilled water, 0.4 mL of 25× buffer, 0.1 mL of solution A (NBT) and 0.1 mL of solution R (BCIP). Incubate 30-45 minutes at room temperature. Wash in distilled water. Dry and transfer to a plastic film. The number of spots are counted using a Zeiss image analyzer Each spot corresponds to an individual IFN-γ secreting T cell.

Results

The animals that tested positive on the ELISPOT analysis are shown in FIGS. 1-4. Overall, the results demonstrate that of the animals tested, 2 out of 2 (i.e. 100%) of the animals that received the intranodal administration of the gp100 antigen, and 2 out of 4 (i.e. 50%) of the animals that received the subcutaneous administration of the gp100 antigen had a positive cell mediated immune response.

ELISA Analysis

The ELISA was performed utilizing standard methodology known in the art Briefly, the human gp100 ("hgp100"; produced in Baculovirus) was diluted in coating buffer (carbonate-bicarbonate, pH9.6) and added to 96 wells at 0.5 ug/well. Plates were placed at 4° C. overnight. Plates were then washed and blocking buffer (phosphate buffered saline/0.5% Tween 20/1.0% BSA, pH7.2) was added for 2 hours at 37° C. The plates were then washed and the sera was diluted in dilution buffer (phosphate buffered saline/0.5% Tween 20/0.1 BSA, pH7.2). For this study, monkey sera was diluted to 1:800 and "7" serial 3 fold dilutions were done for each sample tested. The human sera controls were diluted to 1:50 in dilution buffer and "7" serial 2 fold dilutions were performed. Each dilution was done in duplicate. The plates were incubated a further 2 hours at 37° C. The plates were washed and the horse radish peroxidase (HRP)-conjugated anti-human secondary antibody (anti-human Ig whole antibody from sheep (Amersham Life Science, NA933)) diluted 1:100 in dilution buffer was added to the wells and incubated for 1 hour at 37° C. The plates were washed and OPP (o-phenylenediamine dihydrochloride) substrate with $H_2O_2$ in substrate buffer (50 mM phosphate/25 mM citrate, pH 7.2) was added to the wells. For a kinetics ELISA, the plate was read repeatedly (2 minute intervals for 15 minutes) unstopped (without "stop" buffer). Plates were read at 450 nm.

Results

Figure 5:
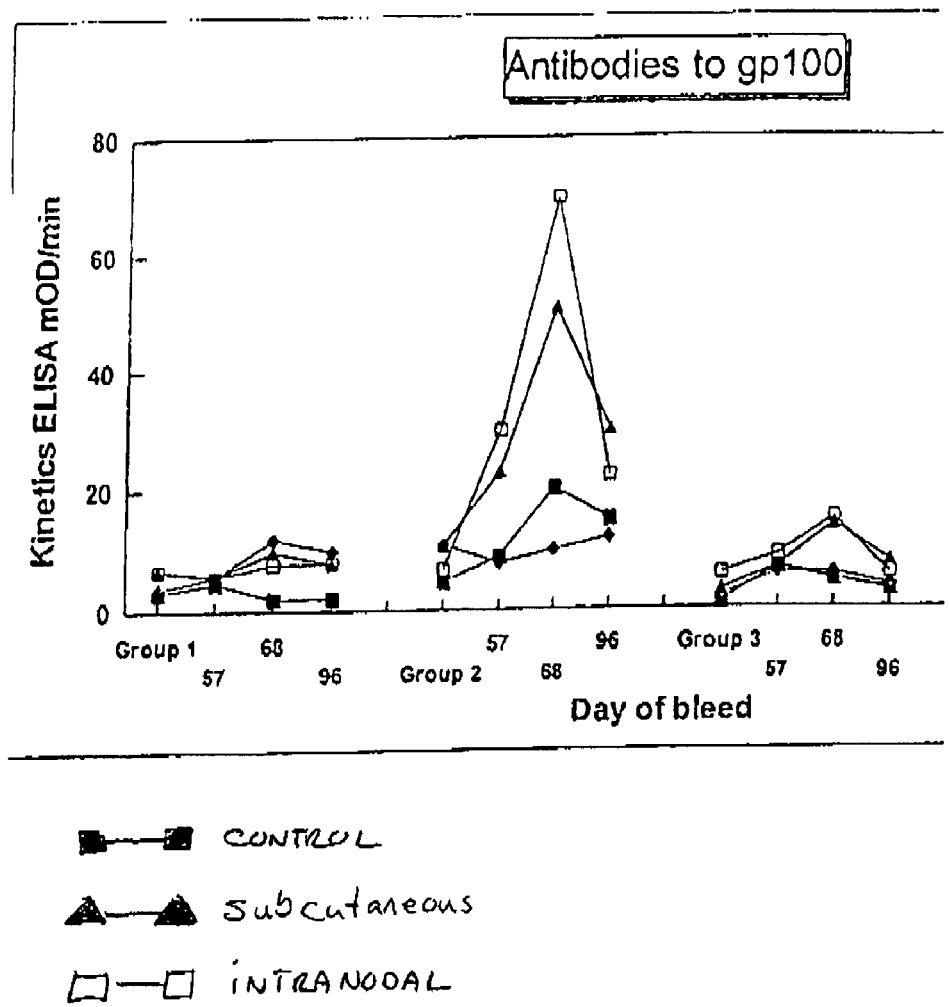
FIG. 5 is a graph showing the antibody response after a regiment of intranodal (group 2) and subcutaneous (group 3) administration of ALVAC-modified gp100/modified gp100 peptide immunogens

The results of the above experiment are presented in Table 8 and in FIG. 5. The animals of group 2 received intranodal injections of ALVAC(2)-gp100(mod) followed by boosts with the modified gp100 peptides 209(2M) and 290(9V); the animals in group 3 received a subcutaneous injection of the ALVAC(2) construct followed by peptide boosts; the animals in group 1 received intranodal injections of saline as a control.

As can be seen from FIG. 5, intranodal injection of the antigens induced a numeral response that was much greater than when the antigen was injected subcutaneously.

In summary, the results of this Example demonstrate that intranodal injection of a tumor antigen induces both a humoral and cell mediated response that is much greater than when the tumor antigen is injected by the conventional subcutaneous route of administration.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| Group Number | Route of administration | Treatment days and compound administered | Number of Animals |
| --- | --- | --- | --- |
| 1 | Intranodal | Saline (NaCl 0.9%): days 28, 42, 56<br>Then 70, 71, 72, 73, 74<br>Then 84, 85, 86, 87 and 88 | 4 |
| 2 | Intranodal | ALVAC(2) - gp100 mod days 28, 42, 56<br>*mgp100 peptides days 70, 71, 72, 73, 74<br>Then 84, 85, 86, 87 and 88 | 4 |

TABLE 1-continued

| Group Number | Route of administration | Treatment days and compound administered | Number of Animals |
|---|---|---|---|
| 3 | Subcutaneous | Saline (NaCl 0.9%) day 1<br>ALVAC(2) - gp100 mod days 28, 42, 56<br>*mgp100 peptides: days 70 and 84 | 4 |

209(2M)-IMDQVPFSY, 290(9V) YLEPGPVTV

*Group 1 animals (control) received the control article (saline for injection (NaCl 0.9%)).

*Group 3 animals received the control article (saline for injection (NaCl 0.9%)) on day 1 only

TABLE 2

| Group Number | Dose level | Dose volume (ml/administration) |
|---|---|---|
| 1 | Saline (NaCl 0.9%): 0 | 0.250 |
| 2 | Dose: 0.25 × 10$^{74}$ CCID 50<br>ALVAC (2) - gp100 mod: 0.25 10$^{74}$ CCID50<br>Dose: 200 µg (Total) of peptides<br>IMDQVPFSY (209(2M)) and<br>YLEPGPVTV (290(9V)) (100 µg each) | 0.250<br>0.2 |
| 3 | Saline (NaCl 0.9%)<br>ALVAC(2) - gp100 mod 0.25 10$^{74}$ CCID 50<br>Dose: 200 µg (Total) of peptides<br>IMDQVPFSY (209(2M)) and<br>YLEPGPVTV (290(9V)) (100 µg each) | 0.250<br>0.250<br>0.2 |

TABLE 3

| Days | Sites used |
|---|---|
| 1 and 28 | lower left |
| 42 | upper left |
| 56 | upper right |
| 70 | lower left |
| 84 | lower right |

TABLE 4

Peptide Pool #1

| Peptide | Sequence | SEQ.ID.NO. |
|---|---|---|
| 1329 | HLAVIGALLAVGATK | SEQ.ID.NO.3 |
| 1330 | GALLAVGATKVPRNQ | SEQ.ID.NO.4 |
| 1331 | VGATKVPRNQDWLGV | SEQ.ID.NO.5 |
| 1332 | VPRNQDWLGVSROLR | SEQ.ID.NO.6 |
| 1333 | DWLGVSRQLRTKAWN | SEQ.ID.NO.7 |
| 1334 | SRQLRTKAWNRQLYP | SEQ.ID.NO.8 |
| 1335 | TKAWNRQLYPEWTEA | SEQ.ID.NO.9 |
| 1336 | RQLYPEWTEAQRLDC | SEQ.ID.NO.10 |
| 1337 | EWTEAQRLDCWRGGQ | SEQ.ID.NO.11 |
| 1338 | QRLDCWRGGOVSLKV | SEQ.ID.NO.12 |
| 1339 | WRGGQVSLKVSNDGP | SEQ.ID.NO.13 |
| 1340 | VSLKVSNDGPTLIGA | SEQ.ID.NO.14 |
| 1344 | IALNFPGSQKVLPDG | SEQ.ID.NO.15 |
| 1345 | PGSQKVLPDGQVIWV | SEQ.ID.NO.16 |
| 1346 | VLPDGQVIWVNNTII | SEQ.ID.NO.17 |
| 1347 | QVIWVNNTIINGSQV | SEQ.ID.NO.18 |
| 1348 | NNTIINGSQVWGGQP | SEQ.ID.NO.19 |
| 1349 | NGSQVWGGQPVYPQE | SEQ.ID.NO.20 |
| 1350 | WGGQPVYPQETDDAC | SEQ.ID.NO.21 |
| 1351 | VYPETDDACIFPDG | SEQ.ID.NO.22 |
| 1352 | TDDACIFPDGGPCPS | SEQ.ID.NO.23 |
| 1353 | IFPDGGPCPSGSWSQ | SEQ.ID.NO.24 |
| 1355 | GSWSQKRSFVYVWKT | SEQ.ID.NO.25 |
| 1356 | KRSFVYVWKTWGQYW | SEQ.ID.NO.26 |
| 1357 | YVWKTWGQYWQVLGG | SEQ.ID.NO.27 |
| 1358 | WGQYWQVLGGPVSGL | SEQ.ID.NO.28 |
| 1359 | QVLGGPVSGLSIGTG | SEQ.ID.NO.29 |

TABLE 5

Peptide Pool #2

| Peptide | Sequence | SEQ.ID.NO. |
|---|---|---|
| 1360 | PVSGLSIGTGRAMLG | SEQ.ID.NO.30 |
| 1361 | SIGTGRAMLGTHTME | SEQ.ID.NO.31 |
| 1362 | RAMLGTHTMEVTVYH | SEQ.ID.NO.32 |
| 1363 | THTMEVTVYHRRGSR | SEQ.ID.NO.33 |
| 1364 | VTVYHRRGSRSYVPI. | SEQ.ID.NO.34 |
| 1365 | RRGSRSYVPLAHSSS | SEQ.ID.NO.35 |
| 1366 | SYVPLAHSSSAFTIT | SEQ.ID.NO.36 |
| 1368 | AFTITDQPFSVSVS | SEQ.ID.NO.37 |
| 1369 | DQVPFSVSVSQLRAL | SEQ.ID.NO.38 |
| 1370 | SVSVSQLRALDGGNK | SEQ.ID.NO.39 |
| 1372 | DGGNKHFLRNQPLTF | SEQ.ID.NO.40 |
| 1373 | HFLRNQPLTFALQLH | SEQ.ID.NO.41 |
| 1374 | QPLTFALQLHDPSGY | SEQ.ID.NO.42 |
| 1375 | ALQLHDPSGYLAEAD | SEQ.ID.NO.43 |
| 1379 | DFGDSSGTLISRALV | SEQ.ID.NO.44 |
| 1380 | STGLISRALVVTHTY | SEQ.ID.NO.45 |
| 1381 | SRALVVTHTYLEPGP | SEQ.ID.NO.46 |
| 1382 | VTHTYLEPGPVTAQV | SEQ.ID.NO.47 |
| 1383 | LEPGPVTAQVVLQAA | SEQ.ID.NO.48 |
| 1384 | VTAQVVLQAAIPLTS | SEQ.ID.NO.49 |
| 1385 | VLQAAIPLTSCGSSP | SEQ.ID.NO.50 |
| 1386 | IPLTSCGSSPVPTT | SEQ.ID.NO.51 |
| 1388 | VPGTTDGHRPTAEAP | SEQ.ID.NO.52 |
| 1389 | DGHRPTAEAPNTTAG | SEQ.ID.NO.53 |
| 1390 | TAEAPNTTAGQVPTT | SEQ.ID.NO.54 |
| 1392 | QVPTTEVVGTTPGQA | SEQ.ID.NO.55 |
| 1393 | EVVGTTPGQAPTAEP | SEQ.ID.NO.56 |

TABLE 6

Peptide Pool #3

| Peptide | Sequence | SEQ.ID.NO. |
|---|---|---|
| 1394 | TPGQAPTAEPSGTTS | SEQ.ID.NO.57 |
| 1395 | PTAEPSGTTSVQVPT | SEQ.ID.NO.58 |
| 1396 | SGTTSVQVPTTEVIS | SEQ.ID.NO.59 |
| 1397 | VQVPTTEVISTAPVQ | SEQ.ID.NO.60 |
| 1398 | TEVISTAPVQMPTAE | SEQ.ID.NO.61 |
| 1399 | TAPVQMPTAESTGMT | SEQ.ID.NO.62 |
| 1400 | MPTAESTGMTPEKVP | SEQ.ID.NO.63 |
| 1401 | STGMTPEKVPVSEVM | SEQ.ID.NO.64 |
| 1402 | PEKVPVSEVMGTTLA | SEQ.ID.NO.65 |
| 1403 | VSEVMGTTLAEMSTP | SEQ.ID.NO.66 |
| 1404 | GTTLAEMSTPEATGM | SEQ.ID.NO.67 |
| 1405 | EMSTPEATGMTPAEV | SEQ.ID.NO.68 |
| 1408 | SIVVLSGTTAAQVTT | SEQ.ID.NO.69 |
| 1409 | SGTTAAQVTTTEWVE | SEQ.ID.NO.70 |
| 1410 | AQVTTTEWVETTARE | SEQ.ID.NO.71 |
| 1411 | TEWVETTARELPIPE | SEQ.ID.NO.72 |
| 1412 | TTARELPIPEPEGPD | SEQ.ID.NO.73 |
| 1413 | LPIPEPEGPDASSIM | SEQ.ID.NO.74 |
| 1414 | PEGPDASSIMSTESI | SEQ.ID.NO.75 |
| 1415 | ASSIMSTESITGSLG | SEQ.ID.NO.76 |
| 1416 | STESITGSLGPLLDG | SEQ.ID.NO.77 |
| 1417 | TGSLGPLLDGTATLR | SEQ.ID.NO.78 |
| 1418 | PLLDGTATLRLVKRQ | SEQ.ID.NO.79 |
| 1419 | TATLRLVKRQVPLDC | SEQ.ID.NO.80 |

TABLE 6-continued

| Peptide Pool #3 | | |
|---|---|---|
| Peptide | Sequence | SEQ.ID.NO. |
| 1420 | LVKRQVPLDCVLYRY | SEQ.ID.NO.81 |
| 1421 | VPLDCVLYRYGSFSV | SEQ.ID.NO.82 |
| 1422 | VLYRYGSFSVTLDIV | SEQ.ID.NO.83 |

TABLE 7

| Peptide Pool #4 | | |
|---|---|---|
| Peptide | Sequence | SEQ.ID.NO. |
| 1424 | TLDIVQGIESAELLQ | SEQ.ID.NO.84 |
| 1425 | QGIESAEILQAVPSG | SEQ.ID.NO.85 |
| 1426 | AEILQAVPSGEGDAF | SEQ.ID.NO.86 |
| 1427 | AVPSGEGDAFELTVS | SEQ.ID.NO.87 |
| 1428 | EGDAFELTVSCQGGL | SEQ.ID.NO.88 |
| 1429 | ELTVSCQGGLPKEAC | SEQ.ID.NO.89 |
| 1430 | CQGGLPKEACMEISS | SEQ.ID.NO.90 |
| 1431 | PKEACMEISSPGCQP | SEQ.ID.NO.91 |
| 1432 | MEISSPGCQPPAQRL | SEQ.ID.NO.92 |
| 1434 | PAQRLCQPVLPSPAC | SEQ.ID.NO.93 |
| 1435 | CQPVLPSPACQLVLH | SEQ.ID.NO.94 |
| 1436 | PSPACQLVLHQILKG | SEQ.ID.NO.95 |
| 1437 | QLVLHQILKGGSGTY | SEQ.ID.NO.96 |
| 1441 | LADTNSLAVVSTQLI | SEQ.ID.NO.97 |
| 1442 | SLAVVSTQLIMPGQE | SEQ.ID.NO.98 |
| 1443 | STQLIMPGQEAGLGQ | SEQ.ID.NO.99 |
| 1444 | MPGQEAGLGQVPLIV | SEQ.ID.NO.100 |
| 1445 | AGLGQVPLIVGILLV | SEQ.ID.NO.101 |

TABLE 7-continued

| Peptide Pool #4 | | |
|---|---|---|
| Peptide | Sequence | SEQ.ID.NO. |
| 1448 | LMAVVLASLIYRRRL | SEQ.ID.NO.102 |
| 1450 | YRRRLMKQDFSVPQL | SEQ.ID.NO.103 |
| 1451 | MKQDFSVPQLPHSSS | SEQ.ID.NO.104 |
| 1452 | SVPQLPHSSSHWLRL | SEQ.ID.NO.105 |
| 1453 | PHSSSHWLRLPRIFC | SEQ.ID.NO.106 |
| 1454 | HWLRLPRIFCSCPIG | SEQ.ID.NO.107 |
| 1455 | PRIFCSCPIGENSPL | SEQ.ID.NO.108 |

TABLE 8

| | DAY (mOD/min) | | | |
|---|---|---|---|---|
| Monkey # | 0 | 57 | 68 | 96 |
| 1 | 3 | 5 | 2 | 2 |
| 2 | 4 | 6 | 12 | 10 |
| 3 | 7 | 6 | 10 | 8 |
| 4 | 7 | 6 | 8 | 8 |
| 5 | 5 | 9 | 20 | 15 |
| 6 | 11 | 8 | 10 | 12 |
| 7 | 11 | 23 | 51 | 30 |
| 8 | 7 | 30 | 70 | 22 |
| 9 | 1 | 7 | 5 | 3 |
| 10 | 2 | 6 | 6 | 4 |
| 11 | 3 | 7 | 14 | 8 |
| 12 | 6 | 9 | 15 | 6 |

We claim:

1. A method for inducing an immune response to a tumor antigen in a human being comprising administering a tumor antigen in a first form directly into at least one lymph node and subsequently administering the tumor antigen in a second form different from the first form directly into the at least one lymph node.

2. A method according to claim 1 wherein the tumor antigen is selected from the group consisting of CEA, gp100, the MAGE family of proteins, DAGE, GAGE, RAGE, NY-ESO 1, Melan-A/MART 1, TRP-1, TRP-2, tyrosinase, HER-2/neu, MUC-1, p53, KSA, PSA, PSMA, fragments thereof and modified versions thereof.

3. A method according to claim 1 wherein at least one of said forms is a nucleic acid encoding the tumor antigen and the nucleic acid is selected from the group consisting of viral nucleic, acid, bacterial DNA, plasmid DNA, naked DNA, and RNA.

4. A method according to claim 3 wherein the viral nucleic acid is selected from the group consisting of adenoviral, alpha viral and poxviral nucleic acid.

5. A method according to claim 4 wherein the poxyiral nucleic acid selected from the group consisting of avipox, orthopox and suipox nucleic acid.

6. A method according to claim 4 wherein the poxyiral nucleic acid is selected from the group consisting of vaccinia, fowl pox, canarypox and swinepox nucleic acid.

7. A method according to claim 4 wherein the poxyiral nucleic acid is selected from the group consisting of MVA, NYVAC, TROVAC, and ALVAC nucleic acid.

8. A method according to claim 1 wherein at least one of said forms is a nucleic acid encoding the tumor antigen and the nucleic acid is contained in a vector.

9. A method according to claim 8 wherein the vector is a recombinant virus or bacteria.

10. A method according to claim 9 wherein the recombinant virus is selected from the group consisting of adenovirus, alphavirus and poxvirus.

11. A method according to claim 10 wherein the poxvirus is selected from the group consisting of avipox, orthopox and suipox.

12. A method according to claim 10 wherein the poxvirus is selected from the group consisting of vaccinia, fowlpox, canarypox and swinepox.

13. A method according to claim 10 wherein the poxvirus is selected from the group consisting of MVA, NYVAC, TROVAC, and ALVAC.

14. A method according to claim 1 wherein at least one of said forms is a nucleic acid encoding the tumor antigen and the nucleic acid is contained in a cell.

15. A method according to claim 1 wherein at least one of said forms is a nucleic acid encoding the tumor antigen and the nucleic acid is contained in a pharmaceutical composition.

16. A method according to claim 1 wherein the tumor antigen is selected from the group consisting of gp100, carcinoembryonic antigen (CEA), a fragment of gp100, a fragment of CEA, a modified version of gp100, and a modified version of CEA.

17. A method according to claim 16 wherein the modified version of gp100 comprises at least the sequence IMDQVPFSY (SEQ ID NO: 1) or the sequence YLEPGPVTV (SEQ. ID NO:2).

18. A method according to claim 16 wherein the modified version of CEA comprises SEQ ID NO:112).

19. A method according to claim 1 wherein the first form is a nucleic, acid and the second form is a peptide.

20. A method according to claim 19 wherein the tumor antigen is selected from the group consisting of CEA, gp100, the MAGE family of proteins, DACE, GAGE, RAGE, NY-ESO 1, Melan-A/MART 1, TRP-1, TRP-2, tyrosinase, HER-2/neu, MUC-1, p53, KSA, PSA, PSMA, fragments thereof, and modified versions thereof.

21. A method according to claim 19 wherein the nucleic acid is selected from the group consisting of viral nucleic acid, bacterial DNA, plasmid DNA, naked DNA, and RNA.

22. A method according to claim 21 wherein the viral nucleic acid is selected from the group consisting of adenoviral, alphaviral and poxyiral nucleic acid.

23. A method according to claim 22 wherein the poxviral nucleic acid selected from the group consisting of avipox, orthopox and suipox nucleic acid.

24. A method according to claim 23 wherein the poxyiral nucleic acid is selected from the group consisting of vaccinia, fowl pox, canarypox and swinepox nucleic acid.

25. A method according to claim 24 wherein the poxyiral nucleic acid is selected from the group consisting of MVA, NYVAC, TROVAC, and ALVAC nucleic acid.

26. The method of claim 1 wherein both a humoral and cell mediated immune response greater than that produced by subcutaneous immunization are observed.

27. The method of claim 1 wherein the tumor antigen is not co-administered with an adjuvant.

28. The method of claim 19 wherein the peptide is selected from the group consisting of SEQ ID NO.: 1, SEQ ID NO.: 2, and SEQ ID NO.: 113.

29. The method of claim 1 wherein the first form of the tumor antigen comprises SEQ ID NO.: 110.

30. The method according to claim 16 wherein the modified version of CEA comprises SEQ ID NO:113.

31. The method of claim 1 wherein the first form of the tumor antigen comprises SEQ ID NO.: 110 and the second form of the tumor antigen is at least one of the peptides SEQ ID NO.: 1 or SEQ ID NO.: 2.

* * * * *

SEQUENCE LISTING

```
<160> NUMBER OF SEQ ID NOS: 113

<210> SEQ ID NO 1
<211> LENGTH: 9
<212> TYPE: PRT
<213> ORGANISM: Human

<400> SEQUENCE: 1

Ile Met Asp Gln Val Pro Phe Ser Tyr
1               5

<210> SEQ ID NO 2
<211> LENGTH: 9
<212> TYPE: PRT
<213> ORGANISM: Human

<400> SEQUENCE: 2

Tyr Leu Glu Pro Gly Pro Val Thr Val
1               5

<210> SEQ ID NO 3
<211> LENGTH: 15
<212> TYPE: PRT
<213> ORGANISM: Human

<400> SEQUENCE: 3

His Leu Ala Val Ile Gly Ala Leu Leu Ala Val Gly Ala Thr Lys
1               5                   10                  15

<210> SEQ ID NO 4
<211> LENGTH: 15
<212> TYPE: PRT
```

-continued

<213> ORGANISM: Human

<400> SEQUENCE: 4

Gly Ala Leu Leu Ala Val Gly Ala Thr Lys Val Pro Arg Asn Gln
1               5                   10                  15

<210> SEQ ID NO 5
<211> LENGTH: 15
<212> TYPE: PRT
<213> ORGANISM: Human

<400> SEQUENCE: 5

Val Gly Ala Thr Lys Val Pro Arg Asn Gln Asp Trp Leu Gly Val
1               5                   10                  15

<210> SEQ ID NO 6
<211> LENGTH: 15
<212> TYPE: PRT
<213> ORGANISM: Human

<400> SEQUENCE: 6

Val Pro Arg Asn Gln Asp Trp Leu Gly Val Ser Arg Gln Leu Arg
1               5                   10                  15

<210> SEQ ID NO 7
<211> LENGTH: 15
<212> TYPE: PRT
<213> ORGANISM: Human

<400> SEQUENCE: 7

Asp Trp Leu Gly Val Ser Arg Gln Leu Arg Thr Lys Ala Trp Asn
1               5                   10                  15

<210> SEQ ID NO 8
<211> LENGTH: 15
<212> TYPE: PRT
<213> ORGANISM: Human

<400> SEQUENCE: 8

Ser Arg Gln Leu Arg Thr Lys Ala Trp Asn Arg Gln Leu Tyr Pro
1               5                   10                  15

<210> SEQ ID NO 9
<211> LENGTH: 15
<212> TYPE: PRT
<213> ORGANISM: Human

<400> SEQUENCE: 9

Thr Lys Ala Trp Asn Arg Gln Leu Tyr Pro Glu Trp Thr Glu Ala
1               5                   10                  15

<210> SEQ ID NO 10
<211> LENGTH: 15
<212> TYPE: PRT
<213> ORGANISM: Human

<400> SEQUENCE: 10

Arg Gln Leu Tyr Pro Glu Trp Thr Glu Ala Gln Arg Leu Asp Cys
1               5                   10                  15

<210> SEQ ID NO 11
<211> LENGTH: 15
<212> TYPE: PRT
<213> ORGANISM: Human

<400> SEQUENCE: 11

```
Glu Trp Thr Glu Ala Gln Arg Leu Asp Cys Trp Arg Gly Gly Gln
1               5                   10                  15

<210> SEQ ID NO 12
<211> LENGTH: 15
<212> TYPE: PRT
<213> ORGANISM: Human

<400> SEQUENCE: 12

Gln Arg Leu Asp Cys Trp Arg Gly Gly Gln Val Ser Leu Lys Val
1               5                   10                  15

<210> SEQ ID NO 13
<211> LENGTH: 15
<212> TYPE: PRT
<213> ORGANISM: Human

<400> SEQUENCE: 13

Trp Arg Gly Gly Gln Val Ser Leu Lys Val Ser Asn Asp Gly Pro
1               5                   10                  15

<210> SEQ ID NO 14
<211> LENGTH: 15
<212> TYPE: PRT
<213> ORGANISM: Human

<400> SEQUENCE: 14

Val Ser Leu Lys Val Ser Asn Asp Gly Pro Thr Leu Ile Gly Ala
1               5                   10                  15

<210> SEQ ID NO 15
<211> LENGTH: 15
<212> TYPE: PRT
<213> ORGANISM: Human

<400> SEQUENCE: 15

Ile Ala Leu Asn Phe Pro Gly Ser Gln Lys Val Leu Pro Asp Gly
1               5                   10                  15

<210> SEQ ID NO 16
<211> LENGTH: 15
<212> TYPE: PRT
<213> ORGANISM: Human

<400> SEQUENCE: 16

Pro Gly Ser Gln Lys Val Leu Pro Asp Gly Gln Val Ile Trp Val
1               5                   10                  15

<210> SEQ ID NO 17
<211> LENGTH: 15
<212> TYPE: PRT
<213> ORGANISM: Human

<400> SEQUENCE: 17

Val Leu Pro Asp Gly Gln Val Ile Trp Val Asn Asn Thr Ile Ile
1               5                   10                  15

<210> SEQ ID NO 18
<211> LENGTH: 15
<212> TYPE: PRT
<213> ORGANISM: Human

<400> SEQUENCE: 18

Gln Val Ile Trp Val Asn Asn Thr Ile Ile Asn Gly Ser Gln Val
1               5                   10                  15
```

```
<210> SEQ ID NO 19
<211> LENGTH: 15
<212> TYPE: PRT
<213> ORGANISM: Human

<400> SEQUENCE: 19

Asn Asn Thr Ile Ile Asn Gly Ser Gln Val Trp Gly Gly Gln Pro
1               5                   10                  15

<210> SEQ ID NO 20
<211> LENGTH: 15
<212> TYPE: PRT
<213> ORGANISM: Human

<400> SEQUENCE: 20

Asn Gly Ser Gln Val Trp Gly Gly Gln Pro Val Tyr Pro Gln Glu
1               5                   10                  15

<210> SEQ ID NO 21
<211> LENGTH: 15
<212> TYPE: PRT
<213> ORGANISM: Human

<400> SEQUENCE: 21

Trp Gly Gly Gln Pro Val Tyr Pro Gln Glu Thr Asp Asp Ala Cys
1               5                   10                  15

<210> SEQ ID NO 22
<211> LENGTH: 15
<212> TYPE: PRT
<213> ORGANISM: Human

<400> SEQUENCE: 22

Val Tyr Pro Gln Glu Thr Asp Asp Ala Cys Ile Phe Pro Asp Gly
1               5                   10                  15

<210> SEQ ID NO 23
<211> LENGTH: 15
<212> TYPE: PRT
<213> ORGANISM: Human

<400> SEQUENCE: 23

Thr Asp Asp Ala Cys Ile Phe Pro Asp Gly Gly Pro Cys Pro Ser
1               5                   10                  15

<210> SEQ ID NO 24
<211> LENGTH: 15
<212> TYPE: PRT
<213> ORGANISM: Human

<400> SEQUENCE: 24

Ile Phe Pro Asp Gly Gly Pro Cys Pro Ser Gly Ser Trp Ser Gln
1               5                   10                  15

<210> SEQ ID NO 25
<211> LENGTH: 15
<212> TYPE: PRT
<213> ORGANISM: Human

<400> SEQUENCE: 25

Gly Ser Trp Ser Gln Lys Arg Ser Phe Val Tyr Val Trp Lys Thr
1               5                   10                  15

<210> SEQ ID NO 26
```

```
<211> LENGTH: 15
<212> TYPE: PRT
<213> ORGANISM: Human

<400> SEQUENCE: 26

Lys Arg Ser Phe Val Tyr Val Trp Lys Thr Trp Gly Gln Tyr Trp
1               5                   10                  15

<210> SEQ ID NO 27
<211> LENGTH: 15
<212> TYPE: PRT
<213> ORGANISM: Human

<400> SEQUENCE: 27

Tyr Val Trp Lys Thr Trp Gly Gln Tyr Trp Gln Val Leu Gly Gly
1               5                   10                  15

<210> SEQ ID NO 28
<211> LENGTH: 15
<212> TYPE: PRT
<213> ORGANISM: Human

<400> SEQUENCE: 28

Trp Gly Gln Tyr Trp Gln Val Leu Gly Gly Pro Val Ser Gly Leu
1               5                   10                  15

<210> SEQ ID NO 29
<211> LENGTH: 15
<212> TYPE: PRT
<213> ORGANISM: Human

<400> SEQUENCE: 29

Gln Val Leu Gly Gly Pro Val Ser Gly Leu Ser Ile Gly Thr Gly
1               5                   10                  15

<210> SEQ ID NO 30
<211> LENGTH: 15
<212> TYPE: PRT
<213> ORGANISM: Human

<400> SEQUENCE: 30

Pro Val Ser Gly Leu Ser Ile Gly Thr Gly Arg Ala Met Leu Gly
1               5                   10                  15

<210> SEQ ID NO 31
<211> LENGTH: 15
<212> TYPE: PRT
<213> ORGANISM: Human

<400> SEQUENCE: 31

Ser Ile Gly Thr Gly Arg Ala Met Leu Gly Thr His Thr Met Glu
1               5                   10                  15

<210> SEQ ID NO 32
<211> LENGTH: 15
<212> TYPE: PRT
<213> ORGANISM: Human

<400> SEQUENCE: 32

Arg Ala Met Leu Gly Thr His Thr Met Glu Val Thr Val Tyr His
1               5                   10                  15

<210> SEQ ID NO 33
<211> LENGTH: 15
<212> TYPE: PRT
<213> ORGANISM: Human
```

```
<400> SEQUENCE: 33

Thr His Thr Met Glu Val Thr Val Tyr His Arg Arg Gly Ser Arg
1               5                   10                  15

<210> SEQ ID NO 34
<211> LENGTH: 15
<212> TYPE: PRT
<213> ORGANISM: Human

<400> SEQUENCE: 34

Val Thr Val Tyr His Arg Arg Gly Ser Arg Ser Tyr Val Pro Leu
1               5                   10                  15

<210> SEQ ID NO 35
<211> LENGTH: 15
<212> TYPE: PRT
<213> ORGANISM: Human

<400> SEQUENCE: 35

Arg Arg Gly Ser Arg Ser Tyr Val Pro Leu Ala His Ser Ser Ser
1               5                   10                  15

<210> SEQ ID NO 36
<211> LENGTH: 15
<212> TYPE: PRT
<213> ORGANISM: Human

<400> SEQUENCE: 36

Ser Tyr Val Pro Leu Ala His Ser Ser Ser Ala Phe Thr Ile Thr
1               5                   10                  15

<210> SEQ ID NO 37
<211> LENGTH: 15
<212> TYPE: PRT
<213> ORGANISM: Human

<400> SEQUENCE: 37

Ala Phe Thr Ile Thr Asp Gln Val Pro Phe Ser Val Ser Val Ser
1               5                   10                  15

<210> SEQ ID NO 38
<211> LENGTH: 15
<212> TYPE: PRT
<213> ORGANISM: Human

<400> SEQUENCE: 38

Asp Gln Val Pro Phe Ser Val Ser Val Ser Gln Leu Arg Ala Leu
1               5                   10                  15

<210> SEQ ID NO 39
<211> LENGTH: 15
<212> TYPE: PRT
<213> ORGANISM: Human

<400> SEQUENCE: 39

Ser Val Ser Val Ser Gln Leu Arg Ala Leu Asp Gly Gly Asn Lys
1               5                   10                  15

<210> SEQ ID NO 40
<211> LENGTH: 15
<212> TYPE: PRT
<213> ORGANISM: Human

<400> SEQUENCE: 40
```

```
Asp Gly Gly Asn Lys His Phe Leu Arg Asn Gln Pro Leu Thr Phe
1               5                   10                  15
```

<210> SEQ ID NO 41
<211> LENGTH: 15
<212> TYPE: PRT
<213> ORGANISM: Human

<400> SEQUENCE: 41

```
His Phe Leu Arg Asn Gln Pro Leu Thr Phe Ala Leu Gln Leu His
1               5                   10                  15
```

<210> SEQ ID NO 42
<211> LENGTH: 15
<212> TYPE: PRT
<213> ORGANISM: Human

<400> SEQUENCE: 42

```
Gln Pro Leu Thr Phe Ala Leu Gln Leu His Asp Pro Ser Gly Tyr
1               5                   10                  15
```

<210> SEQ ID NO 43
<211> LENGTH: 15
<212> TYPE: PRT
<213> ORGANISM: Human

<400> SEQUENCE: 43

```
Ala Leu Gln Leu His Asp Pro Ser Gly Tyr Leu Ala Glu Ala Asp
1               5                   10                  15
```

<210> SEQ ID NO 44
<211> LENGTH: 15
<212> TYPE: PRT
<213> ORGANISM: Human

<400> SEQUENCE: 44

```
Asp Phe Gly Asp Ser Ser Gly Thr Leu Ile Ser Arg Ala Leu Val
1               5                   10                  15
```

<210> SEQ ID NO 45
<211> LENGTH: 15
<212> TYPE: PRT
<213> ORGANISM: Human

<400> SEQUENCE: 45

```
Ser Thr Gly Leu Ile Ser Arg Ala Leu Val Val Thr His Thr Tyr
1               5                   10                  15
```

<210> SEQ ID NO 46
<211> LENGTH: 15
<212> TYPE: PRT
<213> ORGANISM: Human

<400> SEQUENCE: 46

```
Ser Arg Ala Leu Val Val Thr His Thr Tyr Leu Glu Pro Gly Pro
1               5                   10                  15
```

<210> SEQ ID NO 47
<211> LENGTH: 15
<212> TYPE: PRT
<213> ORGANISM: Human

<400> SEQUENCE: 47

```
Val Thr His Thr Tyr Leu Glu Pro Gly Pro Val Thr Ala Gln Val
1               5                   10                  15
```

```
<210> SEQ ID NO 48
<211> LENGTH: 15
<212> TYPE: PRT
<213> ORGANISM: Human

<400> SEQUENCE: 48

Leu Glu Pro Gly Pro Val Thr Ala Gln Val Val Leu Gln Ala Ala
1               5                   10                  15

<210> SEQ ID NO 49
<211> LENGTH: 15
<212> TYPE: PRT
<213> ORGANISM: Human

<400> SEQUENCE: 49

Val Thr Ala Gln Val Val Leu Gln Ala Ala Ile Pro Leu Thr Ser
1               5                   10                  15

<210> SEQ ID NO 50
<211> LENGTH: 15
<212> TYPE: PRT
<213> ORGANISM: Human

<400> SEQUENCE: 50

Val Leu Gln Ala Ala Ile Pro Leu Thr Ser Cys Gly Ser Ser Pro
1               5                   10                  15

<210> SEQ ID NO 51
<211> LENGTH: 15
<212> TYPE: PRT
<213> ORGANISM: Human

<400> SEQUENCE: 51

Ile Pro Leu Thr Ser Cys Gly Ser Ser Pro Val Pro Gly Thr Thr
1               5                   10                  15

<210> SEQ ID NO 52
<211> LENGTH: 15
<212> TYPE: PRT
<213> ORGANISM: Human

<400> SEQUENCE: 52

Val Pro Gly Thr Thr Asp Gly His Arg Pro Thr Ala Glu Ala Pro
1               5                   10                  15

<210> SEQ ID NO 53
<211> LENGTH: 15
<212> TYPE: PRT
<213> ORGANISM: Human

<400> SEQUENCE: 53

Asp Gly His Arg Pro Thr Ala Glu Ala Pro Asn Thr Thr Ala Gly
1               5                   10                  15

<210> SEQ ID NO 54
<211> LENGTH: 15
<212> TYPE: PRT
<213> ORGANISM: Human

<400> SEQUENCE: 54

Thr Ala Glu Ala Pro Asn Thr Thr Ala Gly Gln Val Pro Thr Thr
1               5                   10                  15

<210> SEQ ID NO 55
<211> LENGTH: 15
```

<212> TYPE: PRT
<213> ORGANISM: Human

<400> SEQUENCE: 55

Gln Val Pro Thr Thr Glu Val Val Gly Thr Thr Pro Gly Gln Ala
1               5                   10                  15

<210> SEQ ID NO 56
<211> LENGTH: 15
<212> TYPE: PRT
<213> ORGANISM: Human

<400> SEQUENCE: 56

Glu Val Val Gly Thr Thr Pro Gly Gln Ala Pro Thr Ala Glu Pro
1               5                   10                  15

<210> SEQ ID NO 57
<211> LENGTH: 15
<212> TYPE: PRT
<213> ORGANISM: Human

<400> SEQUENCE: 57

Thr Pro Gly Gln Ala Pro Thr Ala Glu Pro Ser Gly Thr Thr Ser
1               5                   10                  15

<210> SEQ ID NO 58
<211> LENGTH: 15
<212> TYPE: PRT
<213> ORGANISM: Human

<400> SEQUENCE: 58

Pro Thr Ala Glu Pro Ser Gly Thr Thr Ser Val Gln Val Pro Thr
1               5                   10                  15

<210> SEQ ID NO 59
<211> LENGTH: 15
<212> TYPE: PRT
<213> ORGANISM: Human

<400> SEQUENCE: 59

Ser Gly Thr Thr Ser Val Gln Val Pro Thr Thr Glu Val Ile Ser
1               5                   10                  15

<210> SEQ ID NO 60
<211> LENGTH: 15
<212> TYPE: PRT
<213> ORGANISM: Human

<400> SEQUENCE: 60

Val Gln Val Pro Thr Thr Glu Val Ile Ser Thr Ala Pro Val Gln
1               5                   10                  15

<210> SEQ ID NO 61
<211> LENGTH: 15
<212> TYPE: PRT
<213> ORGANISM: Human

<400> SEQUENCE: 61

Thr Glu Val Ile Ser Thr Ala Pro Val Gln Met Pro Thr Ala Glu
1               5                   10                  15

<210> SEQ ID NO 62
<211> LENGTH: 15
<212> TYPE: PRT
<213> ORGANISM: Human

```
<400> SEQUENCE: 62

Thr Ala Pro Val Gln Met Pro Thr Ala Glu Ser Thr Gly Met Thr
1               5                   10                  15

<210> SEQ ID NO 63
<211> LENGTH: 15
<212> TYPE: PRT
<213> ORGANISM: Human

<400> SEQUENCE: 63

Met Pro Thr Ala Glu Ser Thr Gly Met Thr Pro Glu Lys Val Pro
1               5                   10                  15

<210> SEQ ID NO 64
<211> LENGTH: 15
<212> TYPE: PRT
<213> ORGANISM: Human

<400> SEQUENCE: 64

Ser Thr Gly Met Thr Pro Glu Lys Val Pro Val Ser Glu Val Met
1               5                   10                  15

<210> SEQ ID NO 65
<211> LENGTH: 15
<212> TYPE: PRT
<213> ORGANISM: Human

<400> SEQUENCE: 65

Pro Glu Lys Val Pro Val Ser Glu Val Met Gly Thr Thr Leu Ala
1               5                   10                  15

<210> SEQ ID NO 66
<211> LENGTH: 15
<212> TYPE: PRT
<213> ORGANISM: Human

<400> SEQUENCE: 66

Val Ser Glu Val Met Gly Thr Thr Leu Ala Glu Met Ser Thr Pro
1               5                   10                  15

<210> SEQ ID NO 67
<211> LENGTH: 15
<212> TYPE: PRT
<213> ORGANISM: Human

<400> SEQUENCE: 67

Gly Thr Thr Leu Ala Glu Met Ser Thr Pro Glu Ala Thr Gly Met
1               5                   10                  15

<210> SEQ ID NO 68
<211> LENGTH: 15
<212> TYPE: PRT
<213> ORGANISM: Human

<400> SEQUENCE: 68

Glu Met Ser Thr Pro Glu Ala Thr Gly Met Thr Pro Ala Glu Val
1               5                   10                  15

<210> SEQ ID NO 69
<211> LENGTH: 15
<212> TYPE: PRT
<213> ORGANISM: Human

<400> SEQUENCE: 69

Ser Ile Val Val Leu Ser Gly Thr Thr Ala Ala Gln Val Thr Thr
```

```
                1               5                  10                 15
```

<210> SEQ ID NO 70
<211> LENGTH: 15
<212> TYPE: PRT
<213> ORGANISM: Human

<400> SEQUENCE: 70

```
Ser Gly Thr Thr Ala Ala Gln Val Thr Thr Thr Glu Trp Val Glu
1               5                  10                 15
```

<210> SEQ ID NO 71
<211> LENGTH: 15
<212> TYPE: PRT
<213> ORGANISM: Human

<400> SEQUENCE: 71

```
Ala Gln Val Thr Thr Thr Glu Trp Val Glu Thr Thr Ala Arg Glu
1               5                  10                 15
```

<210> SEQ ID NO 72
<211> LENGTH: 15
<212> TYPE: PRT
<213> ORGANISM: Human

<400> SEQUENCE: 72

```
Thr Glu Trp Val Glu Thr Thr Ala Arg Glu Leu Pro Ile Pro Glu
1               5                  10                 15
```

<210> SEQ ID NO 73
<211> LENGTH: 15
<212> TYPE: PRT
<213> ORGANISM: Human

<400> SEQUENCE: 73

```
Thr Thr Ala Arg Glu Leu Pro Ile Pro Glu Pro Glu Gly Pro Asp
1               5                  10                 15
```

<210> SEQ ID NO 74
<211> LENGTH: 15
<212> TYPE: PRT
<213> ORGANISM: Human

<400> SEQUENCE: 74

```
Leu Pro Ile Pro Glu Pro Glu Gly Pro Asp Ala Ser Ser Ile Met
1               5                  10                 15
```

<210> SEQ ID NO 75
<211> LENGTH: 15
<212> TYPE: PRT
<213> ORGANISM: Human

<400> SEQUENCE: 75

```
Pro Glu Gly Pro Asp Ala Ser Ser Ile Met Ser Thr Glu Ser Ile
1               5                  10                 15
```

<210> SEQ ID NO 76
<211> LENGTH: 15
<212> TYPE: PRT
<213> ORGANISM: Human

<400> SEQUENCE: 76

```
Ala Ser Ser Ile Met Ser Thr Glu Ser Ile Thr Gly Ser Leu Gly
1               5                  10                 15
```

-continued

```
<210> SEQ ID NO 77
<211> LENGTH: 15
<212> TYPE: PRT
<213> ORGANISM: Human

<400> SEQUENCE: 77

Ser Thr Glu Ser Ile Thr Gly Ser Leu Gly Pro Leu Leu Asp Gly
1               5                   10                  15

<210> SEQ ID NO 78
<211> LENGTH: 15
<212> TYPE: PRT
<213> ORGANISM: Human

<400> SEQUENCE: 78

Thr Gly Ser Leu Gly Pro Leu Leu Asp Gly Thr Ala Thr Leu Arg
1               5                   10                  15

<210> SEQ ID NO 79
<211> LENGTH: 15
<212> TYPE: PRT
<213> ORGANISM: Human

<400> SEQUENCE: 79

Pro Leu Leu Asp Gly Thr Ala Thr Leu Arg Leu Val Lys Arg Gln
1               5                   10                  15

<210> SEQ ID NO 80
<211> LENGTH: 15
<212> TYPE: PRT
<213> ORGANISM: Human

<400> SEQUENCE: 80

Thr Ala Thr Leu Arg Leu Val Lys Arg Gln Val Pro Leu Asp Cys
1               5                   10                  15

<210> SEQ ID NO 81
<211> LENGTH: 15
<212> TYPE: PRT
<213> ORGANISM: Human

<400> SEQUENCE: 81

Leu Val Lys Arg Gln Val Pro Leu Asp Cys Val Leu Tyr Arg Tyr
1               5                   10                  15

<210> SEQ ID NO 82
<211> LENGTH: 15
<212> TYPE: PRT
<213> ORGANISM: Human

<400> SEQUENCE: 82

Val Pro Leu Asp Cys Val Leu Tyr Arg Tyr Gly Ser Phe Ser Val
1               5                   10                  15

<210> SEQ ID NO 83
<211> LENGTH: 15
<212> TYPE: PRT
<213> ORGANISM: Human

<400> SEQUENCE: 83

Val Leu Tyr Arg Tyr Gly Ser Phe Ser Val Thr Leu Asp Ile Val
1               5                   10                  15

<210> SEQ ID NO 84
<211> LENGTH: 15
<212> TYPE: PRT
```

```
<213> ORGANISM: Human

<400> SEQUENCE: 84

Thr Leu Asp Ile Val Gln Gly Ile Glu Ser Ala Glu Ile Leu Gln
1               5                   10                  15

<210> SEQ ID NO 85
<211> LENGTH: 15
<212> TYPE: PRT
<213> ORGANISM: Human

<400> SEQUENCE: 85

Gln Gly Ile Glu Ser Ala Glu Ile Leu Gln Ala Val Pro Ser Gly
1               5                   10                  15

<210> SEQ ID NO 86
<211> LENGTH: 15
<212> TYPE: PRT
<213> ORGANISM: Human

<400> SEQUENCE: 86

Ala Glu Ile Leu Gln Ala Val Pro Ser Gly Glu Gly Asp Ala Phe
1               5                   10                  15

<210> SEQ ID NO 87
<211> LENGTH: 15
<212> TYPE: PRT
<213> ORGANISM: Human

<400> SEQUENCE: 87

Ala Val Pro Ser Gly Glu Gly Asp Ala Phe Glu Leu Thr Val Ser
1               5                   10                  15

<210> SEQ ID NO 88
<211> LENGTH: 15
<212> TYPE: PRT
<213> ORGANISM: Human

<400> SEQUENCE: 88

Glu Gly Asp Ala Phe Glu Leu Thr Val Ser Cys Gln Gly Gly Leu
1               5                   10                  15

<210> SEQ ID NO 89
<211> LENGTH: 15
<212> TYPE: PRT
<213> ORGANISM: Human

<400> SEQUENCE: 89

Glu Leu Thr Val Ser Cys Gln Gly Gly Leu Pro Lys Glu Ala Cys
1               5                   10                  15

<210> SEQ ID NO 90
<211> LENGTH: 15
<212> TYPE: PRT
<213> ORGANISM: Human

<400> SEQUENCE: 90

Cys Gln Gly Gly Leu Pro Lys Glu Ala Cys Met Glu Ile Ser Ser
1               5                   10                  15

<210> SEQ ID NO 91
<211> LENGTH: 15
<212> TYPE: PRT
<213> ORGANISM: Human

<400> SEQUENCE: 91
```

```
Pro Lys Glu Ala Cys Met Glu Ile Ser Ser Pro Gly Cys Gln Pro
1               5                   10                  15
```

<210> SEQ ID NO 92
<211> LENGTH: 15
<212> TYPE: PRT
<213> ORGANISM: Human

<400> SEQUENCE: 92

```
Met Glu Ile Ser Ser Pro Gly Cys Gln Pro Ala Gln Arg Leu
1               5                   10                  15
```

<210> SEQ ID NO 93
<211> LENGTH: 15
<212> TYPE: PRT
<213> ORGANISM: Human

<400> SEQUENCE: 93

```
Pro Ala Gln Arg Leu Cys Gln Pro Val Leu Pro Ser Pro Ala Cys
1               5                   10                  15
```

<210> SEQ ID NO 94
<211> LENGTH: 15
<212> TYPE: PRT
<213> ORGANISM: Human

<400> SEQUENCE: 94

```
Cys Gln Pro Val Leu Pro Ser Pro Ala Cys Gln Leu Val Leu His
1               5                   10                  15
```

<210> SEQ ID NO 95
<211> LENGTH: 15
<212> TYPE: PRT
<213> ORGANISM: Human

<400> SEQUENCE: 95

```
Pro Ser Pro Ala Cys Gln Leu Val Leu His Gln Ile Leu Lys Gly
1               5                   10                  15
```

<210> SEQ ID NO 96
<211> LENGTH: 15
<212> TYPE: PRT
<213> ORGANISM: Human

<400> SEQUENCE: 96

```
Gln Leu Val Leu His Gln Ile Leu Lys Gly Gly Ser Gly Thr Tyr
1               5                   10                  15
```

<210> SEQ ID NO 97
<211> LENGTH: 15
<212> TYPE: PRT
<213> ORGANISM: Human

<400> SEQUENCE: 97

```
Leu Ala Asp Thr Asn Ser Leu Ala Val Val Ser Thr Gln Leu Ile
1               5                   10                  15
```

<210> SEQ ID NO 98
<211> LENGTH: 15
<212> TYPE: PRT
<213> ORGANISM: Human

<400> SEQUENCE: 98

```
Ser Leu Ala Val Val Ser Thr Gln Leu Ile Met Pro Gly Gln Glu
1               5                   10                  15
```

```
<210> SEQ ID NO 99
<211> LENGTH: 15
<212> TYPE: PRT
<213> ORGANISM: Human

<400> SEQUENCE: 99

Ser Thr Gln Leu Ile Met Pro Gly Gln Glu Ala Gly Leu Gly Gln
1               5                   10                  15

<210> SEQ ID NO 100
<211> LENGTH: 15
<212> TYPE: PRT
<213> ORGANISM: Human

<400> SEQUENCE: 100

Met Pro Gly Gln Glu Ala Gly Leu Gly Gln Val Pro Leu Ile Val
1               5                   10                  15

<210> SEQ ID NO 101
<211> LENGTH: 15
<212> TYPE: PRT
<213> ORGANISM: Human

<400> SEQUENCE: 101

Ala Gly Leu Gly Gln Val Pro Leu Ile Val Gly Ile Leu Leu Val
1               5                   10                  15

<210> SEQ ID NO 102
<211> LENGTH: 15
<212> TYPE: PRT
<213> ORGANISM: Human

<400> SEQUENCE: 102

Leu Met Ala Val Val Leu Ala Ser Leu Ile Tyr Arg Arg Arg Leu
1               5                   10                  15

<210> SEQ ID NO 103
<211> LENGTH: 15
<212> TYPE: PRT
<213> ORGANISM: Human

<400> SEQUENCE: 103

Tyr Arg Arg Arg Leu Met Lys Gln Asp Phe Ser Val Pro Gln Leu
1               5                   10                  15

<210> SEQ ID NO 104
<211> LENGTH: 15
<212> TYPE: PRT
<213> ORGANISM: Human

<400> SEQUENCE: 104

Met Lys Gln Asp Phe Ser Val Pro Gln Leu Pro His Ser Ser Ser
1               5                   10                  15

<210> SEQ ID NO 105
<211> LENGTH: 15
<212> TYPE: PRT
<213> ORGANISM: Human

<400> SEQUENCE: 105

Ser Val Pro Gln Leu Pro His Ser Ser Ser His Trp Leu Arg Leu
1               5                   10                  15

<210> SEQ ID NO 106
```

-continued

```
<211> LENGTH: 15
<212> TYPE: PRT
<213> ORGANISM: Human

<400> SEQUENCE: 106

Pro His Ser Ser His Trp Leu Arg Leu Pro Arg Ile Phe Cys
1               5                   10                  15

<210> SEQ ID NO 107
<211> LENGTH: 15
<212> TYPE: PRT
<213> ORGANISM: Human

<400> SEQUENCE: 107

His Trp Leu Arg Leu Pro Arg Ile Phe Cys Ser Cys Pro Ile Gly
1               5                   10                  15

<210> SEQ ID NO 108
<211> LENGTH: 15
<212> TYPE: PRT
<213> ORGANISM: Human

<400> SEQUENCE: 108

Pro Arg Ile Phe Cys Ser Cys Pro Ile Gly Glu Asn Ser Pro Leu
1               5                   10                  15

<210> SEQ ID NO 109
<211> LENGTH: 1986
<212> TYPE: DNA
<213> ORGANISM: Human

<400> SEQUENCE: 109
atggatctgg tgctaaaaag atgccttctt catttggctg tgataggtgc tttgctggct      60 gtggggcta caaaagtacc cagaaaccag gactggcttg gtgtctcaag gcaactcaga     120
accaaagcct ggaacaggca gctgtatcca gagtggacag aagcccagag acttgactgc     180
tggagaggtg gtcaagtgtc cctcaaggtc agtaatgatg ggcctacact gattggtgca     240
aatgcctcct tctctattgc cttgaacttc cctggaagcc aaaaggtatt gccagatggg     300
caggttatct gggtcaacaa taccatcatc aatgggagcc aggtgtgggg aggacagcca     360
gtgtatcccc aggaaactga cgatgcctgc atcttccctg atggtggacc ttgcccatct     420
ggctcttggt ctcagaagag aagctttgtt tatgtctgga gacctgggg ccaatactgg      480 caagttctag ggggcccagt gtctgggctg agcattggga caggcagggc aatgctgggc     540
acacacacga tggaagtgac tgtctaccat cgccgggat cccggagcta tgtgcctctt      600
gctcattcca gctcagcctt caccattatg gaccaggtgc ctttctccgt gagcgtgtcc     660
cagttgcggg ccttggatgg agggaacaag cacttcctga gaaatcagcc tctgacctt      720 gccctccagc tccatgaccc cagtggctat ctggctgaag ctgacctctc ctacacctgg     780
gactttggag acagtagtgg aacctgatc tctcgggcac ttgtggtcac tcatacttac      840
ctggagcctg gcccagtcac tgttcaggtg gtcctgcagg ctgccattcc tctcacctcc     900
tgtggctcct ccccagttcc aggcaccaca gatgggcaca ggccaactgc agaggcccct     960
aacaccacag ctggccaagt gcctactaca gaagttgtgg gtactacacc tggtcaggcg    1020
ccaactgcag agccctctgg aaccacatct gtgcaggtgc caaccactga agtcataagc    1080
actgcacctg tgcagatgcc aactgcagag agcacaggta tgacacctga aggtgccca    1140 gtttcagagg tcatgggtac cacactgca gagatgtcaa ctccagaggc tacaggtatg    1200
acacctgcag aggtatcaat tgtggtgctt tctggaacca cagctgcaca ggtaacaact    1260
```

```
acagagtggg tggagaccac agctagagag ctacctatcc ctgagcctga aggtccagat    1320
gccagctcaa tcatgtctac ggaaagtatt acaggttccc tgggcccct gctggatggt     1380 acagccacct taaggctggt gaagagacaa gtcccctgg attgtgttct gtatcgatat     1440
ggttcctttt ccgtcaccct ggacattgtc cagggtattg aaagtgccga gatcctgcag    1500
gctgtgccgt ccggtgaggg ggatgcattt gagctgactg tgtcctgcca aggcgggctg    1560
cccaaggaag cctgcatgga gatctcatcg ccagggtgcc agccccctgc ccagcggctg    1620
tgccagcctg tgctacccag cccagcctgc cagctggttc tgcaccagat actgaagggt    1680
ggctcgggga catactgcct caatgtgtct ctggctgata ccaacagcct ggcagtggtc    1740
agcacccagc ttatcatgcc tggtcaagaa gcaggccttg gcaggttcc gctgatcgtg     1800 ggcatcttgc tggtgttgat ggctgtggtc cttgcatctc tgatatatag gcgcagactt    1860
atgaagcaag acttctccgt accccagttg ccacatagca gcagtcactg gctgcgtcta    1920
ccccgcatct tctgctcttg tcccattggt gagaacagcc ccctcctcag tgggcagcag    1980
gtctga                                                               1986
```

<210> SEQ ID NO 110
<211> LENGTH: 661
<212> TYPE: PRT
<213> ORGANISM: Human

<400> SEQUENCE: 110

```
Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr His Thr
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
        195                 200                 205

Ile Met Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240
```

-continued

```
Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Val
        275                 280                 285

Gln Val Val Leu Gln Ala Ala Ile Pro Leu Thr Ser Cys Gly Ser Ser
    290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
        355                 360                 365

Ala Glu Ser Thr Gly Met Thr Pro Glu Lys Val Pro Val Ser Glu Val
    370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
            420                 425                 430

Ile Pro Glu Pro Glu Gly Pro Asp Ala Ser Ser Ile Met Ser Thr Glu
        435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
            500                 505                 510

Thr Val Ser Cys Gln Gly Gly Leu Pro Lys Glu Ala Cys Met Glu Ile
        515                 520                 525

Ser Ser Pro Gly Cys Gln Pro Pro Ala Gln Arg Leu Cys Gln Pro Val
    530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
        595                 600                 605

Val Val Leu Ala Ser Leu Ile Tyr Arg Arg Arg Leu Met Lys Gln Asp
    610                 615                 620

Phe Ser Val Pro Gln Leu Pro His Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
            660
```

<210> SEQ ID NO 111
<211> LENGTH: 2106
<212> TYPE: DNA
<213> ORGANISM: Human

<400> SEQUENCE: 111

| | | | | | |
|---|---|---|---|---|---|
| atggagtctc | cctcggcccc | tccccacaga | tggtgcatcc | cctggcagag | gctcctgctc       60 |
| acagcctcac | ttctaacctt | ctggaacccg | cccaccactg | ccaagctcac | tattgaatcc      120 |
| acgccgttca | atgtcgcaga | ggggaaggag | gtgcttctac | ttgtccacaa | tctgccccag      180 |
| catcttttg  | gctacagctg | gtacaaaggt | gaaagagtgg | atggcaaccg | tcaaattata      240 |
| ggatatgtaa | taggaactca | acaagctacc | ccagggcccg | catacagtgg | tcgagagata      300 |
| atataccccca | atgcatccct | gctgatccag | aacatcatcc | agaatgacac | aggattctac      360 |
| accctacacg | tcataaagtc | agatcttgtg | aatgaagaag | caactggcca | gttccgggta      420 |
| tacccggagc | tgcccaagcc | ctccatctcc | agcaacaact | ccaaacccgt | ggaggacaag      480 |
| gatgctgtgg | ccttcacctg | tgaacctgag | actcaggacg | caacctacct | gtggtgggta      540 |
| aacaatcaga | gcctcccggt | cagtcccagg | ctgcagctgt | ccaatggcaa | caggaccctc      600 |
| actctattca | atgtcacaag | aaatgacaca | gcaagctaca | atgtgaaac  | ccagaaccca      660 |
| gtgagtgcca | ggcgcagtga | ttcagtcatc | ctgaatgtcc | tctatggccc | ggatgccccc      720 |
| accatttccc | ctctaaacac | atcttacaga | tcagggaaa  | atctgaacct | ctcctgccac      780 |
| gcagcctcta | acccacctgc | acagtactct | tggtttgtca | atgggacttt | ccagcaatcc      840 |
| acccaagagc | tctttatccc | caacatcact | gtgaataata | gtggatccta | tacgtgccaa      900 |
| gcccataact | cagacactgg | cctcaatagg | accacagtca | cgacgatcac | agtctatgag      960 |
| ccacccaaac | ccttcatcac | cagcaacaac | tccaaccccg | tggaggatga | ggatgctgta     1020 |
| gccttaacct | gtgaacctga | gattcagaac | acaacctacc | tgtggtgggt | aaataatcag     1080 |
| agcctcccgg | tcagtcccag | gctgcagctg | tccaatgaca | caggaccct  | cactctactc     1140 |
| agtgtcacaa | ggaatgatgt | aggacccat  | gagtgtggaa | tccagaacga | attaagtgtt     1200 |
| gaccacagcg | acccagtcat | cctgaatgtc | ctctatggcc | cagacgaccc | caccatttcc     1260 |
| ccctcataca | cctattaccg | tccagggggtg | aacctcagcc | tctcctgcca | tgcagcctct     1320 |
| aacccacctg | cacagtattc | ttggctgatt | gatgggaaca | tccagcaaca | cacacaagag     1380 |
| ctctttatct | ccaacatcac | tgagaagaac | agcggactct | atacctgcca | ggccaataac     1440 |
| tcagccagtg | gccacagcag | gactacagtc | aagacaatca | cagtctctgc | ggagctgccc     1500 |
| aagccctcca | tctccagcaa | caactccaaa | cccgtggagg | acaaggatgc | tgtggccttc     1560 |
| acctgtgaac | ctgaggctca | gaacacaacc | tacctgtggt | gggtaaatgg | tcagagcctc     1620 |
| ccagtcagtc | ccaggctgca | gctgtccaat | ggcaacagga | ccctcactct | attcaatgtc     1680 |
| acaagaaatg | acgcaagagc | ctatgtatgt | ggaatccaga | actcagtgag | tgcaaaccgc     1740 |
| agtgacccag | tcaccctgga | tgtcctctat | gggccggaca | cccccatcat | ttcccccca      1800 |
| gactcgtctt | acctttcggg | agcggacctc | aacctctcct | gccactcggc | tctaacccca     1860 |
| tccccgcagt | attcttggcg | tatcaatggg | ataccgcagc | aacacacaca | agttctcttt     1920 |
| atcgccaaaa | tcacgccaaa | taataacggg | acctatgcct | gttttgtctc | taacttggct     1980 |
| actggccgca | ataattccat | agtcaagagc | atcacagtct | ctgcatctgg | aacttctcct     2040 |
| ggtctctcag | ctggggccac | tgtcggcatc | atgattggag | tgctggttgg | ggttgctctg     2100 |
| atatag     | | | | |              2106 |

<210> SEQ ID NO 112
<211> LENGTH: 701
<212> TYPE: PRT
<213> ORGANISM: Human

<400> SEQUENCE: 112

```
Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
290                 295                 300

Asp Thr Gly Leu Asn Arg Thr Thr Val Thr Thr Ile Thr Val Tyr Glu
305                 310                 315                 320

Pro Pro Lys Pro Phe Ile Thr Ser Asn Asn Ser Asn Pro Val Glu Asp
                325                 330                 335

Glu Asp Ala Val Ala Leu Thr Cys Glu Pro Glu Ile Gln Asn Thr Thr
            340                 345                 350

Tyr Leu Trp Trp Val Asn Asn Gln Ser Leu Pro Val Ser Pro Arg Leu
        355                 360                 365

Gln Leu Ser Asn Asp Asn Arg Thr Leu Thr Leu Leu Ser Val Thr Arg
370                 375                 380
```

```
Asn Asp Val Gly Pro Tyr Glu Cys Gly Ile Gln Asn Glu Leu Ser Val
385                 390                 395                 400

Asp His Ser Asp Pro Val Ile Leu Asn Val Leu Tyr Gly Pro Asp Asp
                405                 410                 415

Pro Thr Ile Ser Pro Ser Tyr Thr Tyr Tyr Arg Pro Gly Val Asn Leu
            420                 425                 430

Ser Leu Ser Cys His Ala Ala Ser Asn Pro Ala Gln Tyr Ser Trp
            435                 440                 445

Leu Ile Asp Gly Asn Ile Gln Gln His Thr Gln Glu Leu Phe Ile Ser
        450                 455                 460

Asn Ile Thr Glu Lys Asn Ser Gly Leu Tyr Thr Cys Gln Ala Asn Asn
465                 470                 475                 480

Ser Ala Ser Gly His Ser Arg Thr Thr Val Lys Thr Ile Thr Val Ser
            485                 490                 495

Ala Glu Leu Pro Lys Pro Ser Ile Ser Ser Asn Asn Ser Lys Pro Val
            500                 505                 510

Glu Asp Lys Asp Ala Val Ala Phe Thr Cys Glu Pro Glu Ala Gln Asn
            515                 520                 525

Thr Thr Tyr Leu Trp Trp Val Asn Gly Gln Ser Leu Pro Val Ser Pro
530                 535                 540

Arg Leu Gln Leu Ser Asn Gly Asn Arg Thr Leu Thr Leu Phe Asn Val
545                 550                 555                 560

Thr Arg Asn Asp Ala Arg Ala Tyr Val Cys Gly Ile Gln Asn Ser Val
            565                 570                 575

Ser Ala Asn Arg Ser Asp Pro Val Thr Leu Asp Val Leu Tyr Gly Pro
            580                 585                 590

Asp Thr Pro Ile Ile Ser Pro Pro Asp Ser Ser Tyr Leu Ser Gly Ala
            595                 600                 605

Asp Leu Asn Leu Ser Cys His Ser Ala Ser Asn Pro Ser Pro Gln Tyr
            610                 615                 620

Ser Trp Arg Ile Asn Gly Ile Pro Gln Gln His Thr Gln Val Leu Phe
625                 630                 635                 640

Ile Ala Lys Ile Thr Pro Asn Asn Gly Thr Tyr Ala Cys Phe Val
            645                 650                 655

Ser Asn Leu Ala Thr Gly Arg Asn Asn Ser Ile Val Lys Ser Ile Thr
            660                 665                 670

Val Ser Ala Ser Gly Thr Ser Pro Gly Leu Ser Ala Gly Ala Thr Val
            675                 680                 685

Gly Ile Met Ile Gly Val Leu Val Gly Val Ala Leu Ile
            690                 695                 700

<210> SEQ ID NO 113
<211> LENGTH: 9
<212> TYPE: PRT
<213> ORGANISM: Human

<400> SEQUENCE: 113

Tyr Leu Ser Gly Ala Asp Leu Asn Leu
1               5
```